(12) United States Patent
Geisberg

(10) Patent No.: US 7,919,331 B2
(45) Date of Patent: Apr. 5, 2011

(54) CHROMATOGRAPHIC TEST STRIPS FOR ONE OR MORE ANALYTES

(75) Inventor: Mark S. Geisberg, Monrovia, CA (US)

(73) Assignee: Silver Lake Research Corporation, Monrovia, CA (US)

( * ) Notice: Subject to any disclaimer, the term of this patent is extended or adjusted under 35 U.S.C. 154(b) by 467 days.

(21) Appl. No.: 11/961,655

(22) Filed: Dec. 20, 2007

(65) Prior Publication Data

US 2008/0153176 A1 Jun. 26, 2008

Related U.S. Application Data

(60) Provisional application No. 60/871,176, filed on Dec. 21, 2006.

(51) Int. Cl.
*G01N 33/53* (2006.01)

(52) U.S. Cl. ........ 436/514; 436/518; 436/536; 436/540; 436/807; 436/7.1; 436/7.5; 436/7.94; 436/970

(58) Field of Classification Search .................. 436/540, 436/518
See application file for complete search history.

(56) References Cited

U.S. PATENT DOCUMENTS

| | | | |
|---|---|---|---|
| 3,857,931 A | 12/1974 | Hager | |
| 4,104,029 A | 8/1978 | Maier, Jr. | |
| 4,168,146 A | 9/1979 | Grubb et al. | |
| 4,181,636 A | 1/1980 | Fischer | |
| 4,264,766 A | 4/1981 | Fischer | |
| 4,313,734 A | 2/1982 | Leuvering et al. | |
| 4,373,932 A | 2/1983 | Gribnau et al. | |
| 4,435,504 A | 3/1984 | Zuk | |
| 4,703,017 A | 10/1987 | Campbell et al. | |
| 4,740,468 A | 4/1988 | Weng et al. | |
| 4,775,636 A | 10/1988 | Moremans et al. | |
| 4,837,168 A | 6/1989 | deJaeger et al. | |
| 4,861,711 A | 8/1989 | Friesen et al. | |
| 4,916,056 A | 4/1990 | Brown, III et al. | |
| 4,954,452 A | 9/1990 | Yost et al. | |
| 4,959,307 A | 9/1990 | Olson | |
| 5,141,875 A | 8/1992 | Kelton et al. | |
| 5,252,459 A | 10/1993 | Tarcha et al. | |
| 5,296,347 A * | 3/1994 | LaMotte, III | 435/5 |
| 5,559,041 A | 9/1996 | Kang et al. | |
| 5,591,645 A | 1/1997 | Rosenstein | |

FOREIGN PATENT DOCUMENTS

| | | |
|---|---|---|
| EP | 0290194 A1 | 11/1988 |
| EP | 0291194 A1 | 11/1988 |
| EP | 0296724 B1 | 12/1988 |
| EP | 0323605 A2 | 7/1989 |
| WO | 9212428 A1 | 7/1992 |
| WO | 9501775 A1 | 1/1995 |
| WO | 95/27081 | 10/1995 |
| WO | 99/30131 | 6/1999 |

(Continued)

OTHER PUBLICATIONS

Gosling, James. Clinical Chemistry. 1990. vol. 36, No. 8, pp. 1408-1427.*

(Continued)

*Primary Examiner* — Bao-Thuy L Nguyen
(74) *Attorney, Agent, or Firm* — Fulbright & Jaworski L.L.P.

(57) ABSTRACT

The invention describes immunochromatographic protocols in which one or more analytes, such as a bacteria or virus, can be assayed utilizing a "sandwich" complex.

10 Claims, 9 Drawing Sheets

FOREIGN PATENT DOCUMENTS

| WO | 02/44729 A1 | 6/2002 |
| WO | 02/053768 A2 | 7/2002 |
| WO | 2006/117574 A2 | 11/2006 |

OTHER PUBLICATIONS

Cutrecasas, "J. Bio. Chem.," 245:3059 (1970).

March et al., "Anal. Biochem.," 60:149, et seq. (1974).

Canaterero et al., "The Absorption Characteristics of Proteins for Polystyrene and Their Significance in Solid Phase Immunoassays," Analytical Biochemistry, 105:375-382, (1980).

Bangs, "Latex Immunoassays," J. Clin. Immunoassays, 13:127-131 (1980).

* cited by examiner

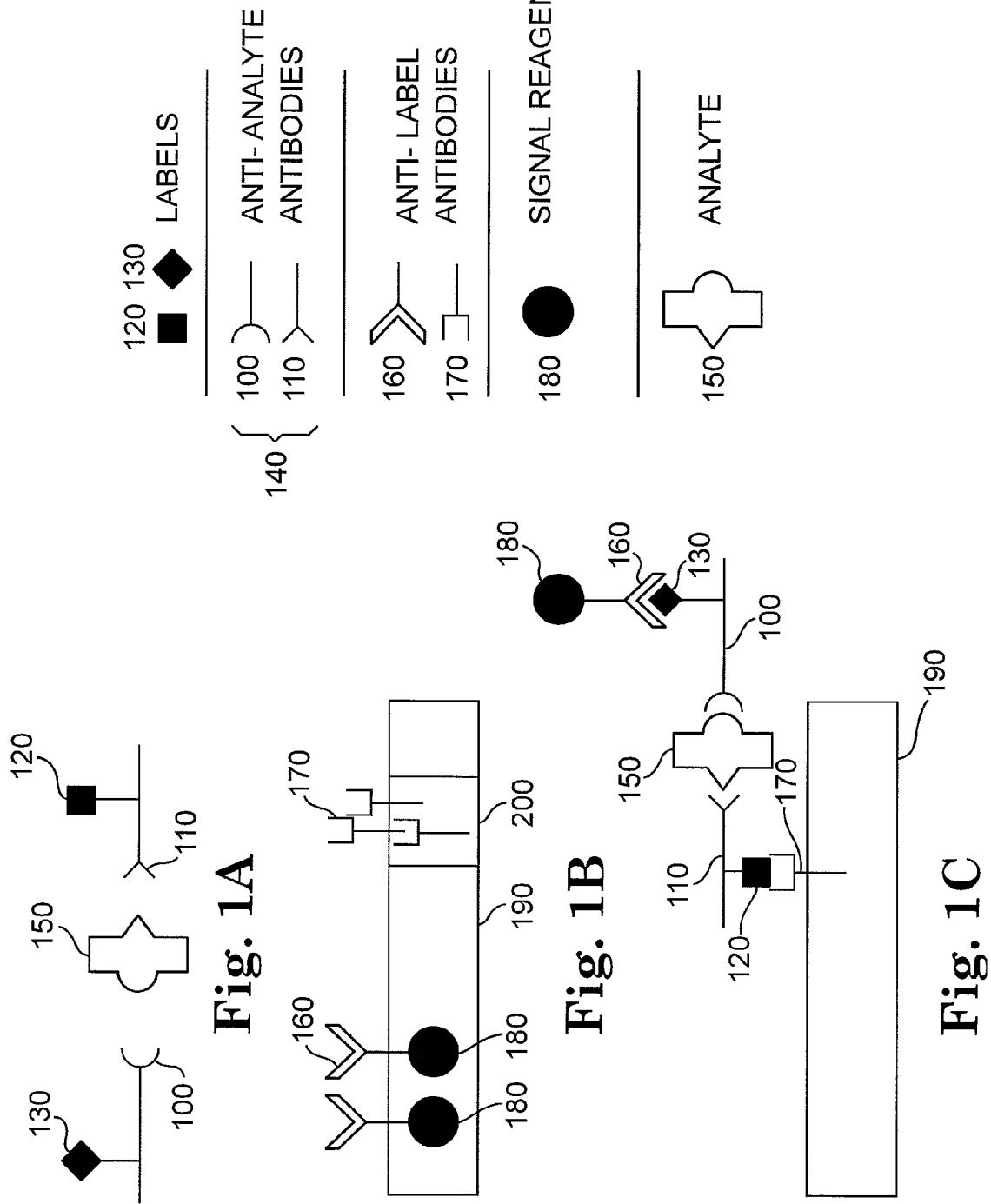

IMMUNOCHROMATOGRAPHIC TEST STRIP DIAGRAM

PLACEMENT OF REAGENTS ON
IMMUNOCHROMATOGRAPHIC TEST STRIP

READOUTS OF RESULTS ON IMMUNOCHROMATOGRAPHIC TET STRIP

CHROMATOGRAPHIC TEST STRIPS FOR ONE OR MORE ANALYTES

CROSS REFERENCE TO RELATED APPLICATIONS

This application also claims benefit under 35 U.S.C. §119 (e) to U.S. Ser. No. 60/871,176, entitled "Immunochromatographic Test Strips", filed Dec. 21, 2006 by Mark Geisberg, the contents of which are incorporated herein by reference in their entirety.

FIELD OF THE INVENTION

The invention relates generally relates to methods, apparatus and compositions, useful for the detection of the presence of an analyte in a liquid sample.

BACKGROUND OF THE INVENTION

One type of ligand-receptor assay is an immunoassay. Various known formats exist for immunoassays, including immunochromatographic test strips for detecting analytes in liquid samples. One format of a ligand-receptor assay uses a direct binding "sandwich" assay, wherein the analyte is bound by two specific binding molecules, the most common type of which is an antibody. Examples of this format are described in U.S. Pat. No. 4,861,711; H. Friesen et al. (1989), which discloses a solid-phase diagnostic device for the determination of biological substances; U.S. Pat. No. 4,740,468; L. Weng et al. (1988) which discloses a solid phase specific binding method and device for detecting an analyte; U.S. Pat. No. 4,168,146; A. Grubb et al. (1979) which discloses a solid phase method and strip with bound antibodies and U.S. Pat. No. 4,435,504; R. Zuk (1984) which discloses a chromatographic immunoassay employing a ligand-binding molecule and a label conjugate.

In one type of this format, described in U.S. Pat. No. 4,959,307; J. Olson (1990), the result is revealed as two lines (positive result) or one line (negative result).

One problem with the dominant format of sandwich-type chromatographic test strips is that antibodies are necessarily bound to a surface when encountering the analyte. Antibodies are covalently or non-covalently bound to the surface of colored particles as well as to fibers of a test strip membrane. These surfaces are not identical in composition or in shape. Attachment of an antibody to either surface is generally deleterious to that antibody's ability to bind antigen, for many reasons including 1. any method of attachment can cause steric hindrance, or blocking of access by the antigen to the antibody's binding sites, 2. deformation of the secondary, tertiary, and quarternary structure of the antibody molecule by the surface causes deleterious changes to the antibody's binding site, 3. dramatically reduced freedom of movement of the antibody in solution decreases the probability kinetics of successful antibody-antigen dockings, 4. non-covalent attachment through hydrophobic-hydrophilic interactions may result in a most-favored configuration that leaves the antibody binding site facing the surface as opposed to facing outward, thus completely hiding the binding sites, 5. covalent attachment adds substantial modifications to the structure of the antibody and may cause even more significant deformations than non-covalent binding, 6. while most antibodies are developed on the basis of optimal binding to antigens while freely dissolved in aqueous solutions, a different kind of binding is required when the antibody is surface-bound, and 7. binding of antibodies to surfaces may change the antibodies' affinity and/or specificity.

These problems are magnified in cases where the concentration of analyte in the sample is low, the affinity or on-rate of the antibody-antigen interaction is suboptimal, or when the samples are complex and present significant potential interferences for the antibody-antigen interaction. Especially in these cases, the decreased probability of a correct antibody-antigen docking can decrease the sensitivity of the assay, increase the background or cross-reactivity, or all of the above.

The second problem associated with the dominant format of the chromatographic test strip is that the format is not well-suited for assays where it is desired to detect any member of a set of analytes. An example of such an assay is a test for bacterial contamination, in which the presence of any of a large number of different bacteria would indicate contamination. In these assays, the optimal design would yield a positive result when any of the analytes were detected or when a group of analytes were detected, without the need to identify which specific analyte was present. An important subset of this kind of assay is a test that shows a positive result when the total number or concentration of several analytes exceeded a threshold level, without regard to the representation of any of the individual analytes within that total number.

In order to create such an assay using the dominant format of the chromatographic test strip, the manufacturer would have to choose several analyte-specific antibodies or pairs of antibodies, couple each to both the signal particles and the membrane, and then carefully calibrate the amounts and ratios of each set to ensure conformity with the sensitivity requirements of the assay. Relative sensitivities of the assay for each analyte are not changeable once the reagent ratios are set. It is exceedingly difficult to fine-tune the affinities, surface binding properties, and total amounts of each reagent in a predictable manner to achieve the performance requirements for a test strip that has a "total number" threshold of several analytes.

In addition, manufacture and quality control of each antibody-signal particle and each antibody on the membrane is considerably laborious and costly for all makers of sandwich-type chromatographic test strips. With multiple such components in a single test strip, this process would dramatically increase manufacturing costs and failure rates of strip tests. Since the failure of one component forces the manufacturer to fail the entire assembly, the cost of manufacture of a multi-analyte test strip is elevated in comparison to a single-analyte test strip.

Furthermore, it is difficult for a maker of a multi-analyte, multi-antibody-pair sandwich-type chromatographic test strip in the dominant format to change the number of analytes or the sensitivity of the test for any individual analyte. The new sensitivity profile necessitates a re-design and re-calibration of each component, especially if new antibody pairs are added.

Partially due to these difficulties, most of the marketed sandwich-type chromatographic test strips are single-analyte assays. In some cases, cross-reactivity of a single polyclonal or monoclonal antibody may enable a single test strip to detect more than one analyte.

Therefore, a need exists for assay that eliminates or reduces one or more of the current drawbacks.

BRIEF SUMMARY OF THE INVENTION

The present invention described herein alleviates one or more of problems that currently exist by creating a new format for chromatographic test strips, where the binding of antibody to antigen takes place in solution phase as an interaction between a single antibody molecule and a single antigen molecule. The advantages of the standard chromatographic test strip format are preserved, including ease of use, visual result readout, and rapid assay time.

Immunochromatographic test strips are provided herein for the detection of analytes in solution. In one format of this method/device, anti-analyte antibodies are bound to a signal reagent (most often, colored particles), and other anti-analyte antibodies are bound to a membrane. When a liquid sample containing the analyte flows through the strip, it dissolves the colored particles, and antibody-analyte binding results in a "sandwich", whereby colored particles are immobilized on the membrane-bound antibodies. A colored signal appears at the site of the membrane-bound antibodies (the "capture zone"), indicating the presence of the analyte in the sample. It should be understood that throughout this specification, the term "antibody" will include all types of ligand-binding molecules—receptors, aptamers, antibody fragments, scFv, etc.

The present format for chromatographic test strips, described herein, provides a facile method for incorporation of multiple anti-analyte antibodies or antibody pairs into a single test strip with a single result. The new format enables incorporation of more than 15 antibody pairs, each pair having specificity for a distinct analyte, and the limit for how many such pairs may be incorporated is unlimited. This invention enables individual calibration of sensitivity for each analyte as well as calibration of sensitivity for the sum total of all analytes in a single result. Additional benefits include cost-effective manufacturing of the tests and the ability to re-calibrate or add analytes without a complete re-design of the test.

In the present format for sandwich-type chromatographic test strips, anti-analyte (antigen) antibodies (referred to as an "analyte binding molecule") are coupled to a label. The label is a small molecule bound, e.g., covalently, to the antibody, so that interference with the antibody binding site is minimal (such conjugation procedures are well-known). In one embodiment, of the two members of an anti-analyte antibody pair, one member is bound to one label (Label A) and the other member is bound to a different label (Label B). The labeled anti-analyte antibodies are allowed to bind to the analyte (antigen) in solution, so that binding events occur between single antibody molecules and single antigen molecules. The solution containing the labelled antibody pair-analyte complex is then exposed sequentially to signal particles coated with anti-Label A antibodies, and then to membrane-bound anti-Label B antibodies in the capture zone. A positive result occurs when signal particles are detected at the capture zone.

In one embodiment, the present invention provides a device for the detection of at least one analyte in a sample solution. The device includes a solid support containing an application zone and a capture zone. The application zone includes components of a first analyte binding molecule (an antibody for example) having a first label, a second analyte binding molecule (another antibody for example) having a second label and a first or second label binding molecule (an antibody selective to the label) containing a signal reagent, wherein the combination of the components forms a complex. The capture zone includes a binding molecule suitable to bind to the remaining uncoupled first or second label binding molecule of the complex, wherein the complex of is in fluid communication with the binding molecule contained within the capture zone.

In another embodiment, the present invention provides a device for the detection of at least one analyte in a sample solution. The device includes a solid support that contains a sample application zone and a capture zone. The sample application zone includes components of an analyte binding molecule having a label and a label binding molecule containing a signal reagent, wherein the combination of the components forms a complex. The capture zone includes an analyte binding molecule wherein the complex is in fluid communication with the analyte binding molecule of the capture zone.

In still another embodiment, the present invention provides a method of detecting an analyte in solution. The method includes the steps of contacting a solution suspected of containing the analyte with a first analyte binding molecule having a first label, a second analyte binding molecule having a second label and a first or second label binding molecule containing a signal reagent, wherein the combination of the components forms a complex. The solution containing the complex is then flowed through a chromatographic test strip to a capture zone. The capture zone includes a binding molecule suitable to bind to the remaining uncoupled first or second label binding molecule of the complex, wherein the complex is in fluid communication with the binding molecule of the capture zone. The presence of the analyte is determined in the solution by the presence of the signal reagent in the capture zone of the chromatographic test strip.

In still yet another embodiment, the present invention provides a method of detecting an analyte in solution. The method includes the steps of: contacting a solution suspected of containing the analyte with an analyte binding molecule having a label and a label binding molecule containing a signal reagent, wherein the combination of the components forms a complex. The solution containing the complex is flowed through a chromatographic test strip to a capture zone. The capture zone includes an analyte binding molecule wherein the complex is in fluid communication with the analyte binding molecule of the capture zone. The presence of the analyte in the solution is determined by the presence of the signal reagent in the capture zone of the chromatographic test strip.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

BRIEF DESCRIPTION OF THE DRAWINGS

FIGS. 1A through 1C illustrate capturing a single analyte on a chromatographic test strip according to the invention.

DETAILED DESCRIPTION

Figure 2A:
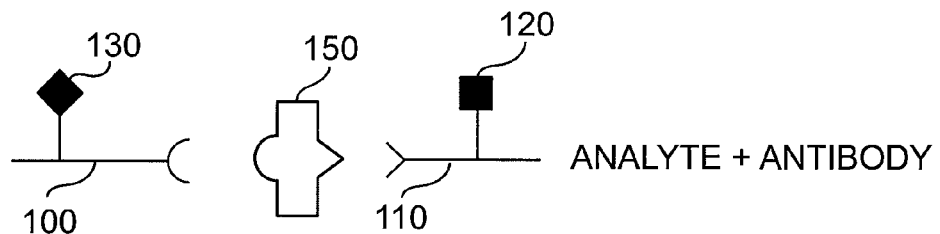
FIGS. 2A through 2C illustrate a similar principal shown in FIGS. 1A through 1C, however, the signal particles are not deposited on the chromatographic test strip but are added to a liquid sample prior to application to the test strip.

Briefly, and as described in more detail below, described herein are methods, compositions and apparatus for detecting the presence of an analyte in a liquid sample.

An "analyte" as used herein is defined primarily by its ability to be a part of a ligand-receptor pair. An analyte as referred to herein can be an antigen but is not necessarily limited to traditional antigens. Analytes include, but are not limited to: microorganisms, such as bacteria and viruses, including indicator bacteria for microbiological assays, infectious disease agents, and biological warfare agents; non-viable microorganisms; proteins, including immunoglobulins, hCG, TSH, LH, FSH, ferritin, CEA, PSA, insulin, hemoglobin, growth hormone, and C-reactive protein; peptides, including hormones, antibiotics, and cytokines; carbohydrates; polymers; and other types of molecular and cellular entities.

"Bibulous" materials are materials that have the capability to effect a chromatographic separation of the contained materials, including paper, nitrocellulose, nylon and the like.

The ligand-receptor (analyte binding molecule and analyte) pair are compounds having spatial and/or polar features which permit the to bind specifically to each other. Ligand-receptor pairs useful in the present invention include specific binding pairs such as antigens and antibodies, or fragments of antibodies (Fab, $Fab_2$, scFv,) both polyclonal and monoclonal, lectins and carbohydrates, hormones and hormone receptors, enzymes and enzyme substrates, biotin and avidin, vitamins and vitamin binding proteins, complementary polynucleotide sequences, drugs and receptors, enzymes and inhibitors, apoproteins and cofactors, growth factors and receptors, aptamers, receptors, and the like. Biotin and avidin derivatives may also be used, including biotin analogs/avidin, biotin/streptavidin, and biotin analogs/streptavidin. Members of ligand-receptor pairs may be "engineered", that is, made by synthetic means. Such techniques are well known in the art, and include techniques for chimeric and humanized antibodies and fragments thereof, synthetic peptides, and synthetic RNA and DNA oligo-nucleotides.

"Liquid Sample" means liquids or extracts obtained from manufacturing lots in the pharmaceutical, food or cosmetic industry, effluents from industrial processes, treated or untreated drinking water or environmental waters, a fluid obtained from any organism or a solid sample obtained from such an organism and the relevant portion extracted or dissolved into a solution, or any other liquid suspected of containing an analyte.

"Non-bibulous" lateral flow means liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components.

"Non-diffusively bound" means the ligand-receptor pairs are either covalently or non-covalently attached to the solid support such that advancing liquid does not cause either member of the pair to substantially move from the place it is applied on the solid support.

"Signal reagent" refers to any of the conventional signaling materials and methods known in the art detectable by methods such as visible inspection, UV and visible spectrophotometry, fluorimetry and radiation counters. Suitable signal reagents include colorable latex particles, such a shown in U.S. Pat. Nos. 4,373,932 and 4,837,168, each incorporated by reference, colloidal metal particles, carbon sol and colored polymer particles. Alternatively the signal reagent can be attached, either covalently or non-covalently, to one or more members of the ligand-receptor pair. Chemiluminescent molecules, such as luminol, luciferin, lucigenin, or oxalyl chloride can be used as a signal reagent, for example as described in U.S. Pat. No. 4,104,029, hereby incorporated by reference herein in its entirety for all purposes. Finally, enzymic systems that react with a colorless substrate to give a colored product, such as horseradish peroxidase and aminoethylcarbazole are also useful as signal reagents.

The particles in the particle zone can be a wide range of materials known in the art. At least one sub-population of these particles is composed of a first member of a ligand-receptor pair and a signal means, as discussed below. Thus, such particles can include enzymes such as glucose oxidase, horseradish peroxidase, alkaline phosphatase, galactosidase, or oxidoreductase. Such an enzyme, along with its signal producing system, such as described in Pawlak et al., International Patent Application No. WO 95/01775 published Jan. 20, 1994, herein incorporated by reference; a carbon sol (as discussed in Kang et al., U.S. Pat. No. 5,559,041, issued Sep. 24, 1996, herein incorporated by reference); erythrocyte ghosts, liposomes, and colored latex particles, (see Campbell et al., U.S. Pat. No. 4,703,017, issued Oct. 27, 1987, and Tarcha et al., U.S. Pat. No. 5,252,459, issued Oct. 12, 1993, both of which are herein incorporated by reference), colloidal metal particles, such as colloidal gold, colloidal silver, colloidal platinum and colloidal selenium (see, for example, Leuvering et al., U.S. Pat. No. 4,313,734, issued Feb. 2, 1982; Moremans et al., U.S. Pat. No. 4,775,636, issued Oct. 4, 1988; Yost et al., U.S. Pat. No. 4,954,452, issued Sep. 4, 1990, all of which are herein incorporated by reference). Colorable particles and colorable latex particles are also known in the art and useful as particles herein (see, for example, Gribnau et al., U.S. Pat. No. 4,373,932, issued Feb. 15, 1983, and de Jaeger et al., U.S. Pat. No. 4,837,168, issued Jun. 6, 1989, respectively, both of which are incorporated herein by reference.) A member of a ligand-receptor pair may be covalently or non-covalently bound to the particles. This binding is accomplished by any method known in the art such as, for example, the use of glutaraldehyde and aminosilanes, as well as other methods described in "Immobilized Enzymes", Ichiro Chibata, Halstead Press, NY (1978); Cutrecasas, J. Bio. Chem., 245:3059 (1970); March et al., Anal. Biochem, 60:149, et seq. (1974); Cantarero et al., "The Absorption Characteristics of Proteins for Polystyrene and Their Significance in Solid phase Immunoassays," Analytical Biochemistry, 105:375-382 (1980); and Bangs, "Latex Immunoassays," J. Clin. Immunoassay, 13:127-131 (1980), Weng et al., U.S. Pat. No. 4,740,468, issued Apr. 26, 1988 (see especially columns 13 through 15); Brown III et al., U.S. Pat. No. 4,916,056, issued Apr. 10, 1990; and U.S. Pat. Nos. 3,857,931; 4,181, 636; and 4,264,766, all of which are incorporated herein by reference.

A "testing substrate" is made of a porous material that is generally hydrophilic or capable of being rendered hydrophilic, including inorganic powders such as silica, magnesium sulfate, and alumina; natural polymeric materials such as cotton, particularly cellulosic materials and materials derived from cellulose, such as fiber containing papers, e.g., filter paper, chromatographic paper, etc.; synthetic or modified naturally occurring polymers, such a nitrocellulose, cellulose acetate, fiberglass, poly(vinyl chloride), polyacrylamide, cross-linked dextran, agarose, polyacrylate, etc.; either used by themselves or in conjunction with other materials; ceramic materials; and the like. Alternatively, the testing substrate of the present invention is fashioned from non-bibulous lateral flow material. Preferably, the testing substrate materials of the present invention are chosen that allow the assay to complete within three minutes of application of the liquid sample.

The shape of the solid support can be that of longitudinal strips, a series of parallel strips, or that of a circular configuration, wherein the circular configuration can optionally be divided into various sections. For the latter configuration, see U.S. Pat. No. 5,141,875, incorporated by reference herein. All that is required is a configuration for which the areas are arranged as discussed above, and that the sample is able to traverse them in the order discussed.

The testing substrate, the chromatographic test strip, may be a porous material having pores of at least about 0.1μ to about 10.0μ, which is susceptible to traversal by an aqueous medium in response to capillary force. Such materials are generally hydrophilic or are capable of being rendered hydrophilic and include inorganic powders such as silica, magnesium sulfate, and alumina; natural polymeric materials such as cotton, particularly cellulosic materials and materials derived from cellulose, such as fiber containing papers, e.g., filter paper, chromatographic paper, etc.; synthetic or modified naturally occurring polymers, such a nitrocellulose, cellulose acetate, fiberglass, poly(vinyl chloride), polyacrylamide, cross-linked dextran, agarose, polyacrylate, etc.; either used by themselves or in conjunction with other materials; ceramic materials; and the like. The testing substrate should not interfere with the signal reagent. This porous material can be attached to rigid or semi-rigid backing. On the other hand, the porous material may provide its own support. The porous material may be polyfunctional or be capable of being polyfunctionalized to permit covalent bonding of members of a ligand-receptor pair, as well as to permit bonding of any other components that are part of the device.

Further examples of the porous testing substrate of the present invention may be found in assays described, for example, in U.S. Pat. Nos. 4,861,711 and 5,591,645, European Patent Publication No. 291,194 and 323,605, each of which is incorporated herein by reference.

Alternatively, the testing substrate of the present invention is fashioned from non-bibulous lateral flow material. By "non-bibulous" lateral flow is meant liquid flow in which all of the dissolved or dispersed components of the liquid are carried at substantially equal rates and with relatively unimpaired flow laterally through the membrane, as opposed to preferential retention of one or more components as would occur, for example, in materials capable of adsorbing or "imbibing" one or more components. "Bibulous" materials include paper, nitrocellulose, nylon and the like, which have the capability to effect a chromatographic separation of the contained materials.

An example of the non-bibulous testing substrate material in which capillary, non-bibulous lateral flow occurs is glass fiber filter, manufactured by a number of suppliers including Whatman PLC of Middlesex, UK. This material has a typical thickness of 0.1-1 mm a density of 25-800 g/m2, and a flow rate of <100 sec/5 cm. There are many other types of materials that have been used for capillary non-bibulous lateral flow, including cellulose, surface-modified cellulose, polyethylene, polyvinyl chloride, polyvinyl acetate, copolymers of vinyl acetate and vinyl chloride, polyamide, polycarbonate, polystyrene, and other polymers. Membranes formed by the classical phase inversion process may also be used. Thus, the non-bibulous solid supports, in general, will be constructed of an inert material and will optimally be less than 1 mm in thickness and allow a capillary flow rate of <100 sec/5 cm.

Bibulous materials can be converted to those which exhibit nonbibulous flow characteristics by the application of blocking agents, in particular certain detergents and proteins, which obscure the interactive forces that account for the bibulous nature of the supports per se. Thus, nonbibulous solid support materials can be comprised of bibulous materials which have been blocked. Preferred blocking agents include bovine serum albumin, either per se or in methylated or succinylated form, whole animal sera, such as horse serum or fetal calf serum, and other blood proteins. Other protein blocking agents include casein and non-fat dry milk. Detergent-based blocking agents can also be used.

Other embodiments of non-bibulous solid support are known in the art and can be found, for example, in Pawlak et al., International Patent Application WO 92/12428, and Sargent et al., European Patent Publication No. 296 724 B1, herein incorporated by reference.

The testing substrate can have a sufficient inherent strength to be used without a backing material, or additional strength can be provided by means of additional backing. The testing substrate can be a single structure such as a sheet cut into strips or it can be particulate material bound to a support or solid surface such as found, for example, in thin-layer chromatography.

A backing is used for support of the testing substrate in some embodiments. The backing preferably is water insoluble, non-porous, and rigid and usually will be of the same length and width as the solid support but can be larger or smaller. A wide variety of organic and inorganic materials, both natural and synthetic, and combinations thereof, can be employed provided only that the backing does not interfere with the capillary action of the strip, or non-specifically bind assay components, or interfere with the signal means. Illustrative materials include polyethylene, polypropylene, poly (4-methylbutene), polystyrene, polymethacrylate, poly(ethylene terephthalate), nylon, poly(vinyl butyrate), glass, ceramics, metals, and the like.

The particular dimensions of the testing substrate will be a matter of convenience, depending upon the size of the sample involved, the assay protocol, the means for detecting and measuring the signal, and the like. For example, the dimensions may be chosen to regulate the rate of fluid migration as well as the amount of sample to be imbibed by porous testing substrate.

Optionally, the testing substrate can be partially or fully enclosed in a moisture-impermeable, inert casing that can be transparent, translucent, or opaque, as known in the art. Such a casing ideally has at least two apertures, one above the sample application zone and one above the signal area(s). The aperture above the signal area(s) can be covered with a transparent material. Alternatively, no apertures above the sample receiving zone are necessary if a bibulous means is provided to the exterior of the casing and to the testing substrate below the sample receiving zone such that the sample would be wicked in and applied to the testing substrate. Examples of such casings can be found in European Patent Publication No. 290 194.

One member of a ligand-receptor pair may be non-diffusively bound by direct or indirect means to the solid support. The solid support may have been previously derivatized prior to the application of the second member. The direct binding can be covalent or non-covalent. Covalent binding can be accomplished by using a solid support derivatized with reactive groups such as amino, chloromethyl, aldehyde, carboxyl, epoxy, and the like. Covalent binding can also be accomplished by any method known in the art such as, for example, the use of glutaraldehyde, aminosilanes, cyanogen bromide, carbonyldiimidazole, ethyl chloroformate, 1-(3-nitrobenzyloxy-methyl)-pyridimium chloride (NBPC) and treslyl chloride, as well as other methods described in "Immobilized Enzymes", Ichiro Chibata, Halstead Press, NY (1978); Cutrecasas, J. Bio. Chem., 245:3059 (1970); March et al., Anal. Biochem., 60:149, et seq. (1974); and Tijssen et al., Practice and Theory of Enzyme Immunoassays, Chapter 3, Elsevier Science Publishers, (1985). The non-covalent binding takes advantage of the natural adhesion of second members to the non-synthetic and especially the synthetic fibers. Thus, appropriately buffered solutions can be mixed with the solid support then evaporated, leaving a coating of the desired member of the ligand-receptor pair on the membrane.

The non-direct method for applying the members to the solid support employs either covalently or non-covalently binding the second members to microparticles. Such microparticles may then be bound to or entrapped by the solid support such that the microparticles are within the matrix of the membrane, on the surface of the membrane, or bound to other microparticles which are in turn bound to the membrane. The size of the microparticles should be such that they do not migrate through the membrane to any significant degree. The microparticles may be made of a variety of naturally-occurring or synthetic materials, such as microparticles are those made from polyethylene, polystyrene, agarose, dextran, cellulose, starch, or the like and the aldehyde, carboxyl, amino, hydroxyl, or hydrazide derivatives thereof. The binding of the member to the microparticle may be by methods similar to those discussed above for binding the second member directly to the solid support or other methods known to those skilled in the art, as discussed above for the preparation of the particles.

The members of a ligand-receptor pair, whether bound to a microparticle or not, can be applied to the solid support by a variety of means known in the art. Various "printing" techniques have previously been proposed for application of such liquid reagents to carriers, for example, micro-syringes, pens using metered pumps, direct printing and ink-jet printing, and any of these techniques can be used in the present context. To facilitate manufacture, the solid support can be treated with the particles and then subdivided into smaller portions (e.g., small, narrow strips each embodying the required areas and zones) to provide a plurality of identical solid supports. In applying the members to the solid support, it is necessary that the signal zone(s) span the width and the depth of the solvent front created by any fluid traversing through the solid support. Such fluid may be the sample solution, a wicking fluid as described below, or a solution containing the substrate for an enzymatic signal means.

Referring now to FIGS. 1A through 7, illustrate methods for detecting analytes in a liquid sample according to various embodiments of the invention.

In one format for the presently inventive sandwich-type chromatographic test strips, FIG. 1A shows anti-analyte antibodies (for example) 100 and 110 are coupled to labels 120 and 130, respectively. The preferred label (120 or 130) is a small molecule covalently bound to the antibody (100 or 110), so that interference with the antibody binding site is minimal (such conjugation procedures are well-known). Multiple label molecules may be attached to each antibody molecule. In one particular embodiment, of the two members of an anti-analyte antibody pair 140, one member is bound to one label (Label 120) and the other member is bound to a different label (Label 130). The labeled anti-analyte antibodies are allowed to bind to the analyte 150 in solution, so that binding events occur between single antibody molecules and single antigen (analyte) molecules. As shown in FIG. 1B, the solution containing the labelled antibody pair—analyte complex is then exposed sequentially to signal reagent 180 coated with anti-Label 120 antibodies (160), and then to membrane 190-bound anti-Label 130 antibodies (170) in the capture zone 200. FIG. 1C provides that a positive result occurs when signal reagents 180, such as visible particles, are detected at the capture zone 200.

FIGS. 1A through 1C show one embodiment of this format, where anti-analyte antibodies 100 and 110, coupled to labels 120 and 130, respectively, are added to the analyte 150—containing liquid sample. These antibodies may be added as a liquid reagent or dried in a sample-receiving container to be rehydrated by addition of the sample. The sample is then applied to the chromatographic test strip 190, where the liquid flows through the strip 190 by capillary diffusion. The liquid dissolves and carries signal reagent 180 (e.g., particles), that were deposited on the test strip 190 and dried, bound to anti-Label 120 antibody 160. When liquid flow reaches the capture zone 200, membrane-bound anti-Label 130 antibodies 170 capture the (signal reagent 180)-(anti-120)-(120-anti-analyte 100)-(analyte 150)-(130-anti-analyte 110) [or 180-160-120-100-150-110-130] complexes to create a visually detectable signal.

Figure 2B:
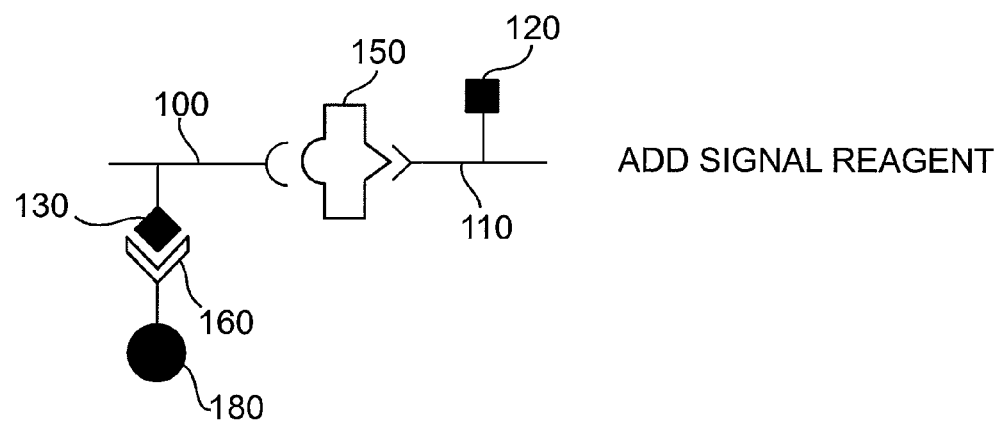
Figure 2C:
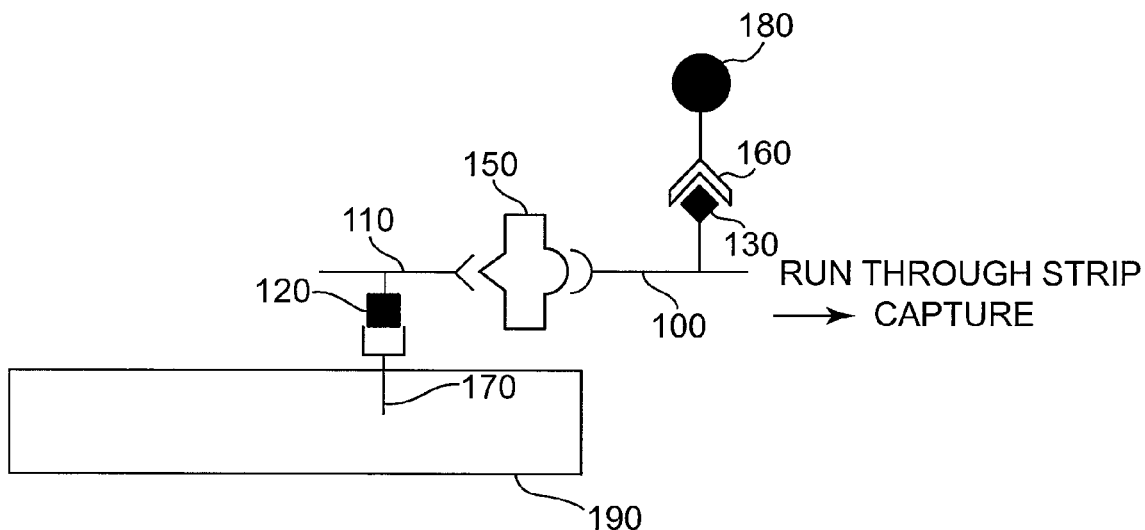

Another embodiment based on the format depicted in FIGS. 1A through 1C is shown in FIGS. 2A through 2C. In this variation, signal reagent 180 bound to anti-Label 120 antibody are not deposited on the chromatographic test strip, rather they are added to the liquid sample either at the same time or after addition of the anti-analyte antibodies. The remainder of the process is equivalent to that of FIGS. 1A through 1C.

Figure 3A:
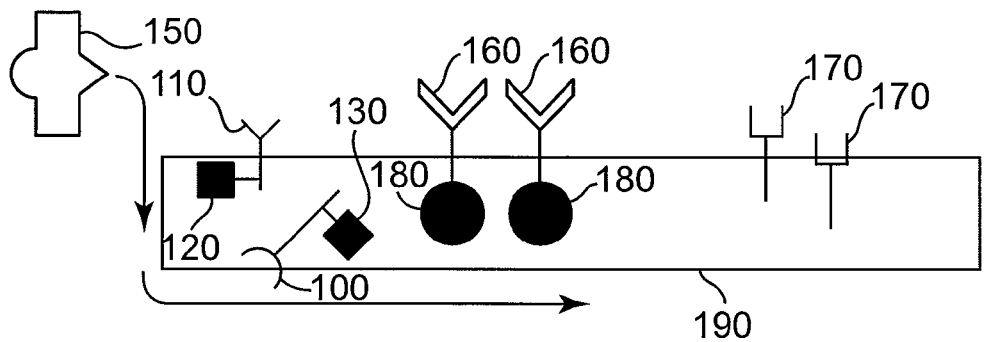
FIGS. 3A through 3C illustrate a similar principal as shown in FIGS. 1A through 1C, however, the reagents are deposited on the test strip and then dried. A solution is then applied to the test strip with an analyte and then eluted.
Figure 3B:
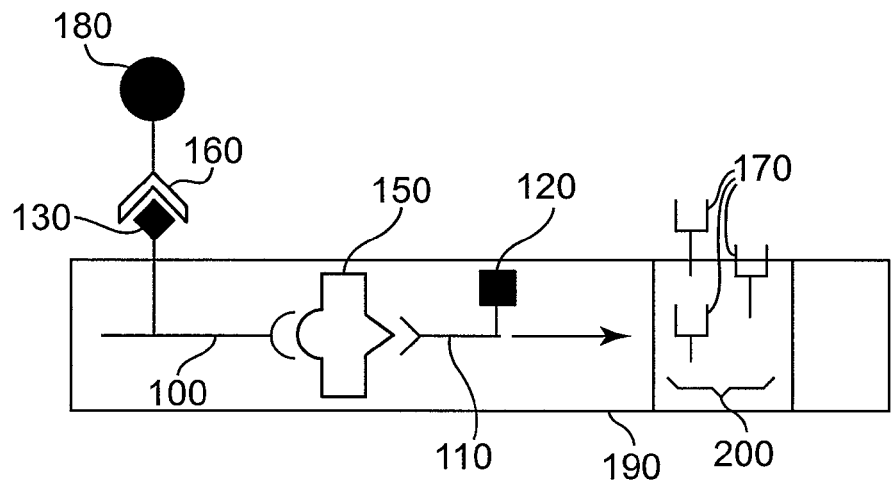
Figure 3C:
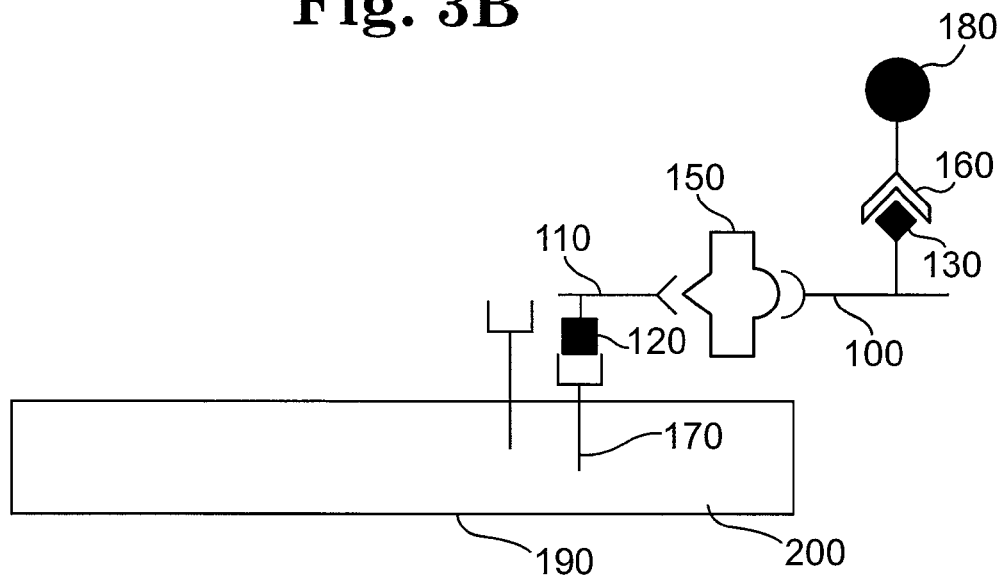

Still another embodiment is shown in FIGS. 3A through 3C. In this variation, all reagents (100-120, 110-130, 160, 170, 180) can be deposited on the chromatographic test strip 190 and dried. The liquid sample, with analyte 150, is applied and rehydrates each reagent sequentially to complete the formation of the (signal reagent 180)-(anti-A)-(A-anti-analyte)-(analyte 150)-(B-anti-analyte) complexes. These complexes are captured in the capture zone 200 by anti-Label B antibodies 170.

Figure 4A:
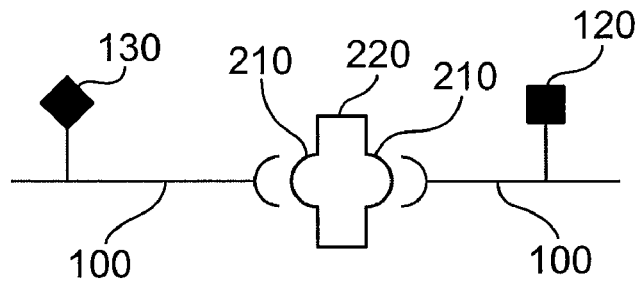
FIGS. 4A through 4C illustrate a poly-epitope analyte, such as a virus or bacteria.
Figure 4B:
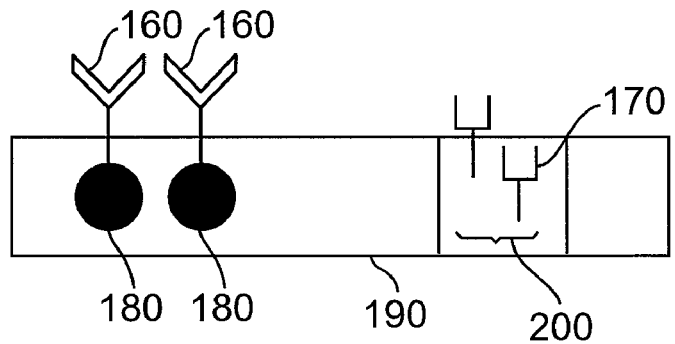
Figure 4C:
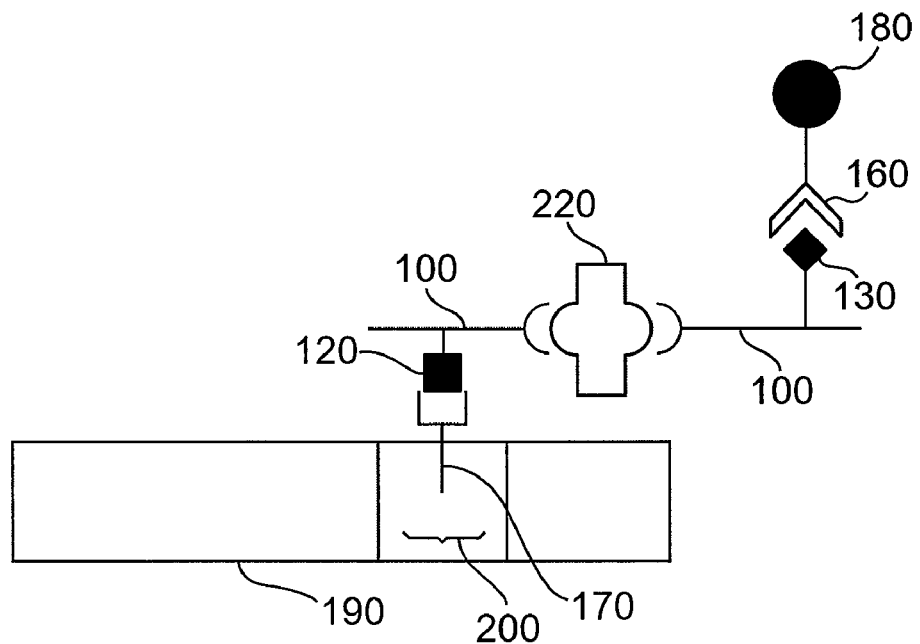

FIGS. 4A through 4C show yet another embodiment of the invention that can be used when the analyte 220 has multiple epitopes 210, including the particular subset of these analytes which has multiple identical epitopes 210. An example of such an analyte 220 is a bacterium or a virus. In this case, a single anti-analyte antibody 100, where some of these antibody molecules are bound to label 120 and others to label 130, is sufficient for the formation of necessary complexes in the capture zone 200. This variation includes the case where a single polyclonal anti-analyte antibody is used, specific for multiple epitopes on a single analyte.

Figure 5A:
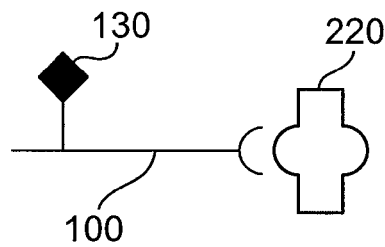
FIGS. 5A through 5C and 6A through 6C illustrate a variation of the invention where a single label is utilized.
Figure 5B:
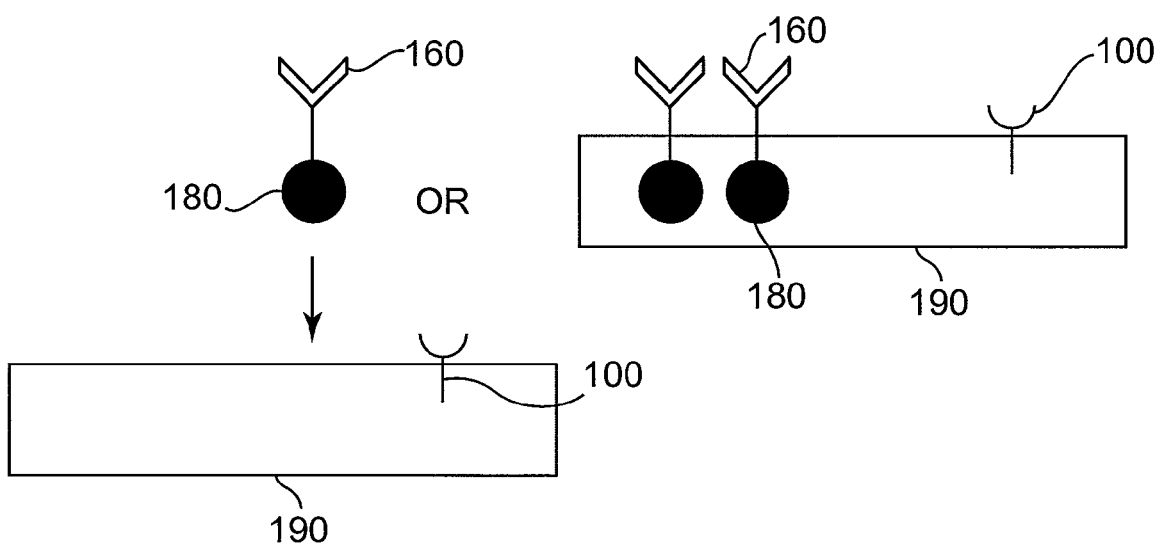
Figure 5C:
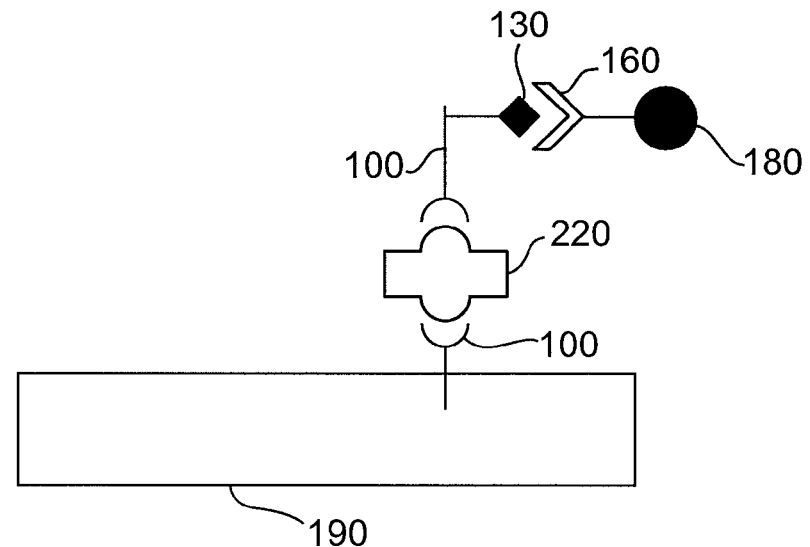
Figure 6A:
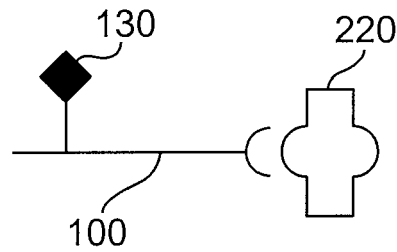
Figure 6B:
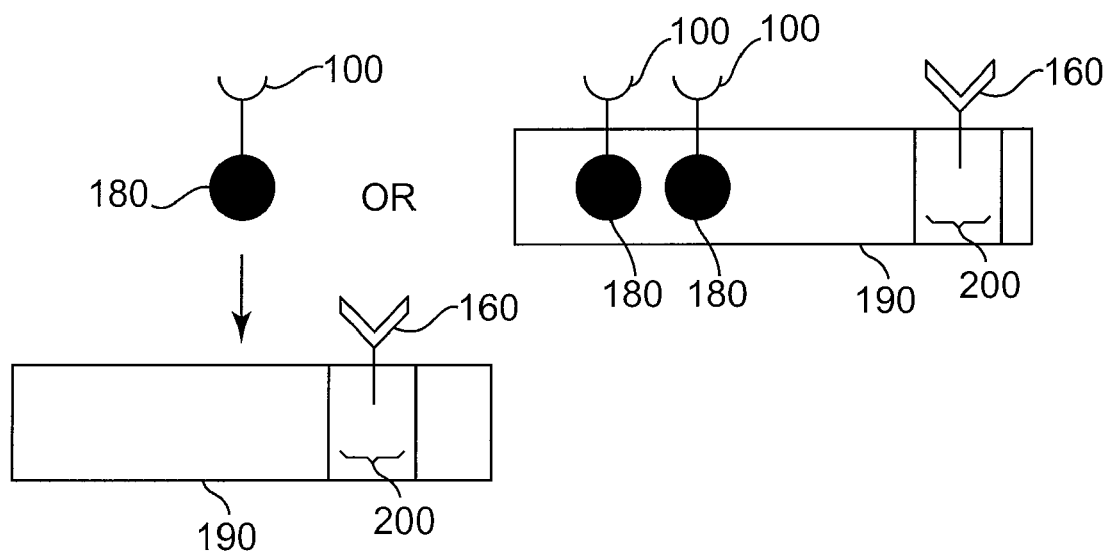
Figure 6C:
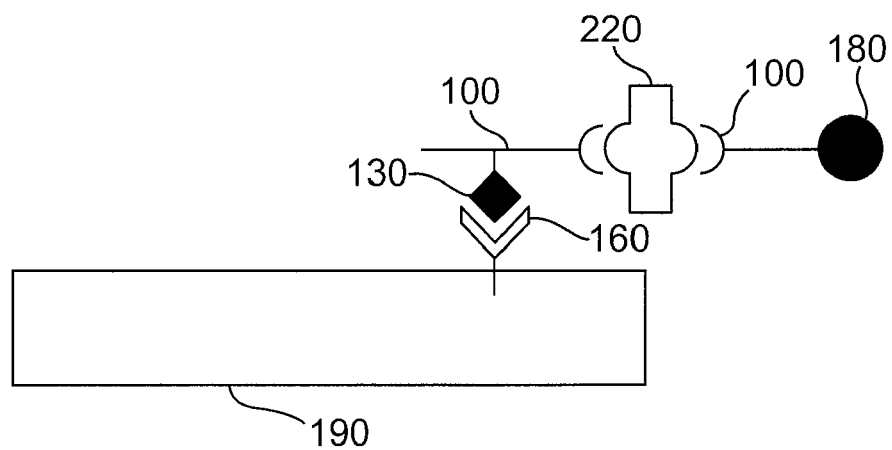

FIGS. 5A through 5C and FIGS. 6A through 6C show yet another embodiment where a single label 130 or 120, respectively, is used. In some cases, it may be advantageous to use an anti-analyte antibody, such as 100 for example (although it should be understood that anti-analyte antibody 110 could be used as well where the epitope 210 of analyte 220 would be suited for the anti-analyte binding site), instead of an anti-label antibody, for either the capture zone or conjugation to the signal reagent 180. There may be cases where an anti-analyte antibody such as 100 is shown to bind adequately when on the surface of the signal reagent, but inadequately when bound to a membrane 190 (or vice-versa). In these cases, it is sufficient to produce a single label-conjugated anti-analyte antibody. FIGS. 5A through 5C illustrate the single-label method when the unlabelled anti-analyte antibody is used for capture. FIGS. 6A through 6C illustrates the single-label method when the unlabelled anti-analyte antibody is bound to the signal reagent.

Combinations of these variations are also possible. FIGS. 1-3 address the formatting of procedure steps and placement of reagents within or outside of the test strip device. FIG. 4 addresses possible anti-analyte antibody variations. FIGS. 5 and 6 address label possibilities. These are independent variables, and each assay may be determined to optimally perform under a different final configuration. In fact, it is expected that every analyte—antibody combination may perform optimally with a different combination.

Figure 7A:
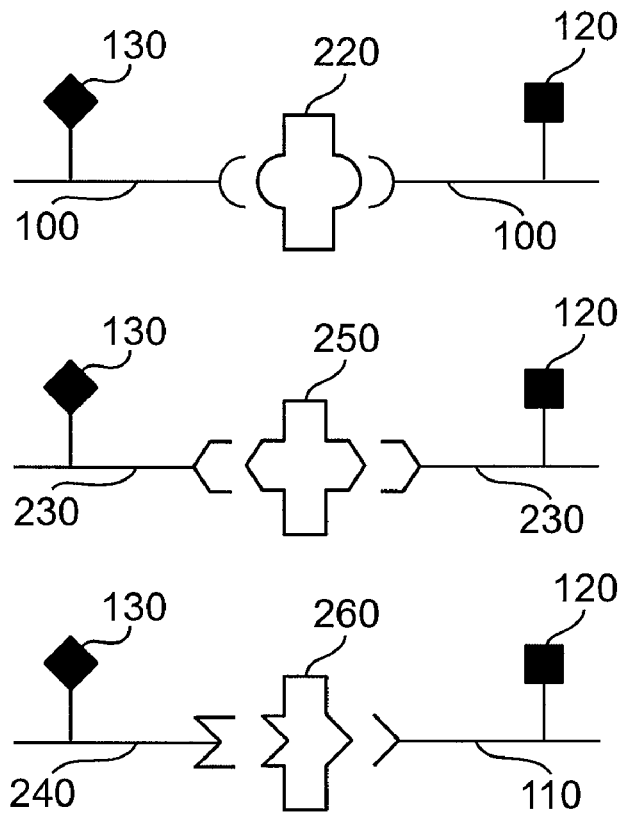
FIGS. 7A through 7C illustrate that the new invention provides the ability to test for multiple analytes in a single assay.
Figure 7B:
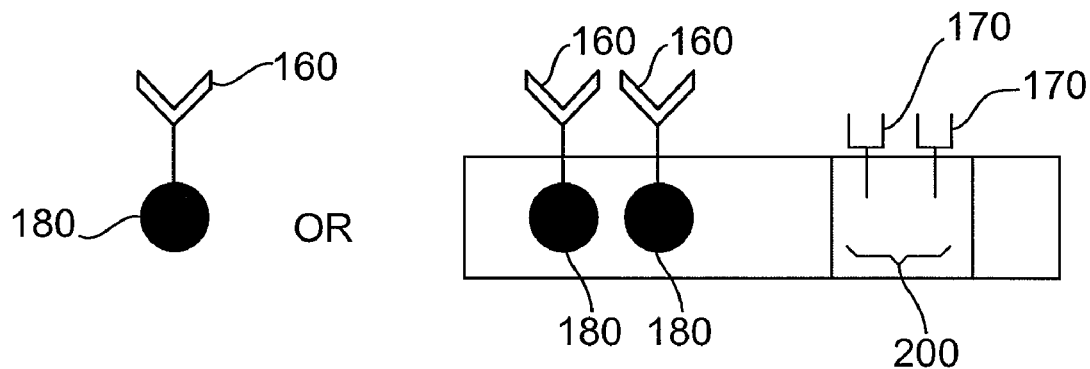

FIG. 7 shows one example of incorporating multiple anti-analyte antibodies 100, 110, 230 and/or 240 into a single assay. In this scenario, there are three analytes 220, 250 and 260, any or all of which may be present in the sample. This example uses three anti-analyte antibody pairs-100-100, 230-230, and 110-240 (Note: analytes 220 and 250 are analogous to FIG. 4, where the analytes are multi-epitope and only one anti-analyte specificity is necessary; analyte 260 is analogous to FIG. 1, where two anti-analyte specificities are needed. Whether one or two specificities are used, the term "antibody pair" refers to two antibodies that can simultaneously bind to a single analyte). One member of each anti-analyte antibody pair is conjugated to label 120, and the other to label 130. The anti-analyte antibodies 100, 110, 230 and 240 are allowed to bind to the analyte (any of 220, 250 and 260) in the sample, followed by the steps described for FIG. 1. The appearance of a signal in the capture zone can be due to the binding of any of the (signal reagent)-(anti-120)-(120-anti-analyte)-(analyte)-(130-anti-analyte) complexes, without differentiation between specific analytes.

The format described in FIG. 7, including the various embodiments, is well suited for assays where any of a set of analytes are to be detected, without necessarily identifying the specific analyte being detected. The formats allow easy integration of multiple antibodies, each capable of binding distinct analytes, into a single assay where the positive result indicates the presence of any of the analytes in any combination yielding a total analyte concentration above the detection limit of the assay.

Figure 7C:
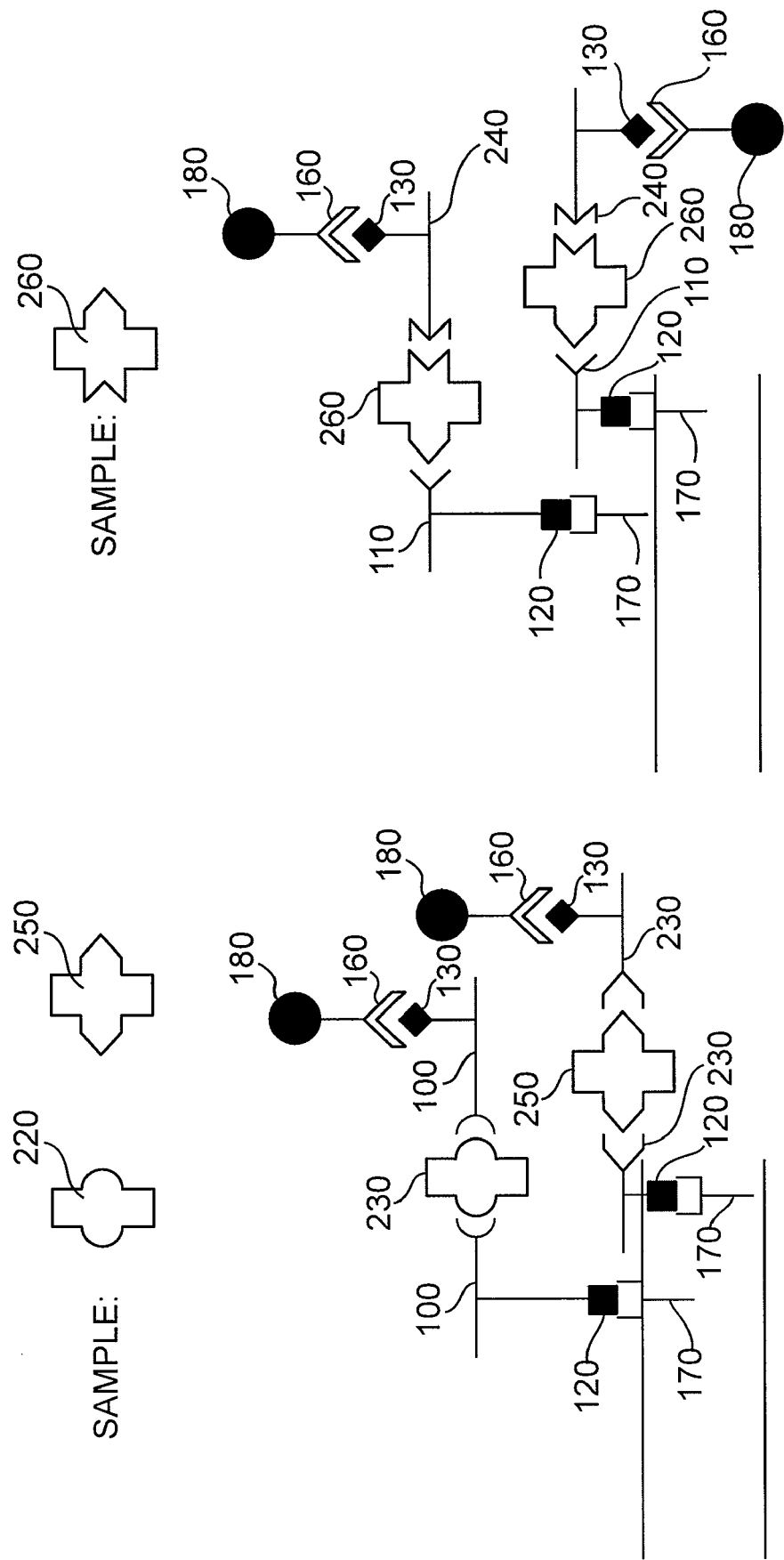

All sandwich-type chromatographic test strip assays have a detection limit, usually the lowest concentration of analyte that results in the appearance of a visible signal at the capture zone. In the case of multiple analytes, the detection limit would be the sum of concentrations of all analytes that results in the appearance of a visible signal at the capture zone. For example, FIG. 7C shows the appearance of a signal when the sample contains a mixture of the first two analytes and when the sample contains only the third analyte.

Any of the embodiments in FIGS. 1-6, or combinations of these embodiments, is adaptable to multiple anti-analyte antibody pairs. The particular embodiment is adapted to multiple analytes by simply substituting a group of anti-analyte antibodies for a single anti-analyte antibody.

There are many important advantages that the present invention includes, however, one particular advantage of this format is the ease of development and manufacturing of the described assays. The format simplifies the functionalities built into the strip, simplifying quality control and eliminating sources of failure. The advantages include, but are not limited to:

1. Anti-label antibodies are selected once and then used for any set of analytes. Anti-analyte antibodies are selected primarily for their ability to bind the analyte, and there is great variation in the performance of these antibodies when conjugated to signal reagent or immobilized on membranes. It is rather straightforward to select a single anti-label antibody that has optimal binding characteristics when attached to a colored particle, or adhered to a nitrocellulose membrane. Once the anti-label antibody is chosen and the optimal binding protocol is determined, this part of the test assembly is no longer a source of significant variability or failure, especially if this anti-label antibody is monoclonal.

2. Anti-analyte antibodies are conjugated to labels through established methods. Conjugation of antibodies to other molecules can be achieved by a variety of well-known and reproducible methods. These procedures have been a cornerstone of immunoassays for many years. Many suppliers offer conjugation kits, which make conjugations simple and cost-effective (e.g., Pierce Biotechnology, Calbiochem, Sigma, etc.). There are simple methods for purification, validation, and quality control of conjugated antibodies. Finally, label-conjugated antibodies can be produced in bulk and are stable for years at standard storage conditions. On the other hand, attachment of antibodies to colored particles or membranes can have poor reproducibility, colloidal suspensions of colored particles are inherently unstable, and scale-up can be problematic.

3. Modular manufacturing of test kits. Signal reagents, test strips, and conjugated antibodies can all be produced and validated independently, even for multi-analyte test kits. Final assembly involves a small number of steps and therefore a low failure rate. In contrast, chromatographic strip test kits in the dominant format are typically assembled from a multitude of analyte-specific components, including (anti-analyte antibody—signal particle) assemblies and (anti-analyte antibody—membrane) components. For multi-analyte test kits, this process can utilize several components of low stability and high failure rate. Since the failure rate of the combined assemblies is a multiplication product of the failure rates of individual components, failure rate for the final assembly can be very high.

It should be understood that the present invention readily lends itself to "kit" preparations, wherein one or more of the reagents can be made available separately and combined to provide the methods and devices described herein. In one embodiment, the reagents can be included in bottles or similar containers and be added to each other and to the sample prior to contact with a solid support. In another embodiment, some or all reagents may be deposited on the solid support, to be rehydrated by sample flow. Typically, the capture zone reagent(s) are already included on the support, prior to contact with the remaining reagents and analyte.

The following paragraphs enumerated consecutively from 1 through 65 provide for various aspects of the present invention. In one embodiment, in a first paragraph (1), the present invention provides a device for the detection of at least one analyte in a sample solution, comprising: a) components comprising a first analyte-binding molecule having a label and a label-binding molecule having a signal reagent, wherein the combination of the components is capable of forming a complex when contacted by fluid comprising an analyte; and b) a solid support comprising a capture zone, the capture zone comprising a second analyte-binding molecule, wherein the complex of (a) is in fluid communication with the analyte-binding molecule of (b).

2. The device of paragraph 1, wherein the first or second analyte-binding molecule is an antibody, an aptamer, a receptor, an antibody fragment, or a polynucleotide.

3. The device of either of paragraphs 1 or 2, wherein the label is biotin and the label-binding molecule is avidin or streptavidin.

4. The device of any of paragraphs 1 through 3, wherein the label is a hapten or polypeptide and the label-binding molecule is an antibody, an antibody fragment, or a receptor capable of binding the hapten or polypeptide.

5. The device of any of paragraphs 1 through 4, wherein the signal reagent is a colored colloidal metal particle, a colored latex particle, or a colored polymer particle.

6. The device of any of paragraphs 1 through 5, wherein the signal reagent is a fluorescent molecule, an enzyme, or a light-emitting molecule.

7. The device of any of paragraphs 1 through 6, wherein at least one member of a set that includes the analyte-binding molecule having a label and the label-binding molecule having a signal reagent is deposited on the solid support.

8. The device of any of paragraphs 1 through 7, wherein the solid support contains a bibulous material, nitrocellulose, or polyvinylidene fluoride.

9. The device of any of paragraphs 1 through 8, wherein the analyte is a microorganism or a group of microorganisms.

10. The device of any of paragraphs 1 through 9, wherein the analyte is one or more members of a set that includes proteins, carbohydrates, and polymers.

11. The device of any of paragraphs 1 through 10, wherein the presence or absence of the analyte is determined visually or spectrophotometrically by the appearance of signal reagent in the capture zone.

12. A device for the detection of an analyte in a sample solution, comprising: a) components comprising an analyte-binding molecule comprising a signal reagent, and an analyte-binding molecule comprising a label, wherein the components are capable of forming a complex with an analyte when contacted by fluid comprising the analyte; and b) a solid support comprising a capture zone, the capture zone comprising a label-binding molecule, wherein the complex of (a) is in fluid communication with the label-binding molecule of (b).

13. The device of paragraph 12, wherein the analyte-binding molecule is an antibody, an aptamer, a receptor, an antibody fragment, or a polynucleotide.

14. The device of either of paragraphs 12 or 13, wherein the label is biotin and the label-binding molecule is avidin or streptavidin.

15. The device of any of paragraphs 12 through 14, wherein the label is a hapten or polypeptide and the label-binding molecule is an antibody, an antibody fragment, or a receptor capable of binding the hapten or polypeptide.

16. The device of any of paragraphs 12 through 15, wherein the signal reagent is a colored colloidal metal particle, a colored latex particle, or a colored polymer particle.

17. The device of any of paragraphs 12 through 16, wherein the signal reagent is a fluorescent molecule, an enzyme, or a light-emitting molecule.

18. The device of any of paragraphs 12 through 17, wherein at least one member of a set that includes the analyte-binding molecule having a label and the analyte-binding molecule having a signal reagent is deposited on the solid support.

19. The device of any of paragraphs 12 through 18, wherein the solid support contains a bibulous material, nitrocellulose, or polyvinylidene fluoride.

20. The device of any of paragraphs 12 through 19, wherein the analyte is a microorganism or a group of microorganisms.

21. The device of any of paragraphs 12 through 20, wherein the analyte is one or more members of a set that includes proteins, carbohydrates, and polymers.

22. The device of any of paragraphs 12 through 21, wherein the presence or absence of the analyte is determined visually or spectrophotometrically by the appearance of signal reagent in the capture zone.

23. A device for the detection of an analyte in a sample solution, comprising: a) components comprising an analyte-binding molecule having a first label, a second analyte-binding molecule having a second label, and a first-label-binding molecule comprising a signal reagent, wherein the combination of the components is capable of forming a complex when contacted by fluid comprising the analyte; and b) a solid support comprising a capture zone, the capture zone comprising a binding molecule suitable to bind to the second label, wherein the complex of (a) is in fluid communication with the binding molecule of (b).

24. The device of paragraph 23, wherein the first or second analyte-binding molecule is an antibody, an aptamer, a receptor, an antibody fragment, or a polynucleotide.

25. The device of either of paragraphs 23 or 24, wherein the first or second label is biotin and the first- or second-label-binding molecule is avidin or streptavidin.

26. The device of any of paragraphs 23 through 25, wherein the first or second label is a hapten or polypeptide and the first- or second-label-binding molecule is an antibody, an antibody fragment, or a receptor capable of binding the hapten or polypeptide.

27. The device of any of paragraphs 23 through 26, wherein the signal reagent is a colored colloidal metal particle, a colored latex particle, or a colored polymer particle.

28. The device of any of paragraphs 23 through 27, wherein the signal reagent is a fluorescent molecule, an enzyme, or a light-emitting molecule.

29. The device of any of paragraphs 23 through 28, wherein at least one member of a set that includes the analyte-binding molecule having a first label, the second analyte-binding molecule having a second label, and a first-label-binding molecule comprising a signal reagent is deposited on the solid support.

30. The device of any of paragraphs 23 through 29, wherein the solid support contains a bibulous material, nitrocellulose, or polyvinylidene fluoride.

31. The device of any of paragraphs 23 through 30, wherein the analyte is a microorganism or a group of microorganisms.

32. The device of any of paragraphs 23 through 31, wherein the analyte is one or more members of a set that includes proteins, carbohydrates, and polymers.

33. The device of any of paragraphs 23 through 32, wherein the presence or absence of the analyte is determined visually or spectrophotometrically by the appearance of signal reagent in the capture zone.

34. A method of detecting an analyte in solution, comprising the steps of: contacting a solution suspected of comprising the analyte with a first analyte-binding molecule having a label and a label-binding molecule having a signal reagent, wherein the combination of the binding molecules is capable of forming a complex (a) when contacted by fluid comprising an analyte; flowing the solution comprising the complex through a chromatographic test strip to a capture zone, wherein the capture zone comprises a second analyte-binding molecule (b); and determining the presence of the analyte in the solution by the presence of the signal reagent in the capture zone of the chromatographic test strip.

35. The method of paragraph 34, wherein the first or second analyte-binding molecule is an antibody, an aptamer, a receptor, an antibody fragment, or a polynucleotide.

36. The method of either of paragraphs 34 or 35, wherein the label is biotin and the label-binding molecule is avidin or streptavidin.

37. The method of any of paragraphs 34 through 36, wherein the label is a hapten or polypeptide and the label-binding molecule is an antibody, an antibody fragment, or a receptor capable of binding the hapten or polypeptide.

38. The method of any of paragraphs 34 through 37, wherein the signal reagent is a colored colloidal metal particle, a colored latex particle, or a colored polymer particle.

39. The method of any of paragraphs 34 through 38, wherein the signal reagent is a fluorescent molecule, an enzyme, or a light-emitting molecule.

40. The method of any of paragraphs 34 through 39, wherein the chromatographic test strip contains a bibulous material, nitrocellulose, or polyvinylidene fluoride.

41. The method of any of paragraphs 34 through 40, wherein the analyte is a microorganism or a group of microorganisms.

42. The method of any of paragraphs 34 through 41, wherein the analyte is one or more members of a set that includes proteins, carbohydrates, and polymers.

43. The method of any of paragraphs 34 through 42, wherein the presence or absence of the analyte is determined visually or spectrophotometrically.

44. A method of detecting an analyte in solution, comprising the steps of: contacting a solution suspected of comprising the analyte with an analyte-binding molecule having a label and an analyte-binding molecule having a signal reagent, wherein the combination of the binding molecules is capable of forming a complex (a) when contacted by fluid comprising an analyte; flowing the solution comprising the complex through a chromatographic test strip to a capture zone, comprising a label-binding molecule (b); and determining the presence of the analyte in the solution by the presence of the signal reagent in the capture zone of the chromatographic test strip.

45. The method of paragraph 44, wherein the first or second analyte-binding molecule is an antibody, an aptamer, a receptor, an antibody fragment, or a polynucleotide.

46. The method of either of paragraphs 44 or 45, wherein the label is biotin and the label-binding molecule is avidin or streptavidin.

47. The method of any of paragraphs 44 through 46, wherein the label is a hapten or polypeptide and the label-binding molecule is an antibody, an antibody fragment, or a receptor capable of binding the hapten or polypeptide.

48. The method of any of paragraphs 44 through 47, wherein the signal reagent is a colored colloidal metal particle, a colored latex particle, or a colored polymer particle.

49. The method of any of paragraphs 44 through 48, wherein the signal reagent is a fluorescent molecule, an enzyme, or a light-emitting molecule.

50. The method of any of paragraphs 44 through 49, wherein the chromatographic test strip contains a bibulous material, nitrocellulose, or polyvinylidene fluoride.

51. The method of any of paragraphs 44 through 50, wherein the analyte is a microorganism or a group of microorganisms.

52. The method of any of paragraphs 44 through 51, wherein the analyte is one or more members of a set that includes proteins, carbohydrates, and polymers.

53. The method of any of paragraphs 44 through 52, wherein the presence or absence of the analyte is determined visually or spectrophotometrically.

54. A method of detecting an analyte in solution, comprising the steps of: contacting a solution suspected of comprising the analyte with a first analyte-binding molecule having a first label, a second analyte-binding molecule having a second label, and a first-label-binding molecule having a signal reagent, wherein the combination of the binding molecules is capable of forming a complex (a) when contacted by fluid comprising an analyte; flowing the solution comprising the complex through a chromatographic test strip to a capture zone, comprising a binding molecule (b) suitable to bind to the second label; and determining the presence of the analyte in the solution by the presence of the signal reagent in the capture zone of the chromatographic test strip.

55. The method of paragraph 54, wherein the first or second analyte-binding molecule is an antibody, an aptamer, a receptor, an antibody fragment, or a polynucleotide.

56. The method of either paragraphs 54 or 55, wherein the first or second label is biotin and the first- or second-label-binding molecule is avidin or streptavidin.

57. The method of any of paragraphs 54 through 56, wherein the first or second label is a hapten or polypeptide and the first- or second-label-binding molecule is an antibody, an antibody fragment, or a receptor capable of binding the hapten or polypeptide.

58. The method of any of paragraphs 54 through 57, wherein the signal reagent is a colored colloidal metal particle, a colored latex particle, or a colored polymer particle.

59. The method of any of paragraphs 54 through 58, wherein the signal reagent is a fluorescent molecule, an enzyme, or a light-emitting molecule.

60. The method of any of paragraphs 54 through 59, wherein the chromatographic test strip contains a bibulous material, nitrocellulose, or polyvinylidene fluoride.

61. The method of any of paragraphs 54 through 60, wherein the analyte is a microorganism or a group of microorganisms.

62. The method of any of paragraphs 54 through 61, wherein the analyte is one or more members of a set that includes proteins, carbohydrates, and polymers.

63. The method of any of paragraphs 54 through 62, wherein the presence or absence of the analyte is determined visually or spectrophotometrically.

64. The device of any of paragraphs 1 through 11 and 23 through 33, wherein the second analyte-binding molecule is the same as the first analyte-binding molecule.

65. The method of any of paragraphs 34 through 43 and 54 through 63, wherein the second analyte-binding molecule is the same as the first analyte-binding molecule.

EXAMPLES

Example 1

Detection of a Single Analyte with a Double-Label System

The following example describes the detection of the bacterium *Escherichia coli* in aqueous samples. The presence of *E. coli* in liquids such as drinking water or fruit juice can be used as an indication of potential toxicity and inadequate disinfection processes. The assay described here is using two anti-*E. coli* antibodies, each coupled to a different label, and an immunochromatographic test strip. In this example, one label is biotin and the other label is a small molecule—the antibiotic streptomycin. The label-binding molecules are streptavidin and a monoclonal antibody to streptomycin.

Production of labelled anti-E. coli antibodies. Rabbits were immunized with heat-killed EC in complete Freund's adjuvant, followed by boosters with EC in incomplete Freund's adjuvant, according to previously described methods (E Harlow and D Lane, Antibodies: A Laboratory Manual (Cold Spring Harbor, N.Y.: CSHL Press, 1988)). Bleeds from two rabbits were combined and the IgG fraction was purified by Protein A chromatography. The resulting anti-E. coli polyclonal antiserum was conjugated to biotin by previously described methods (Pierce Biotechnology, Doc. No. 0237, Instructions for EZ-Link NHS-Biotin, NHS-LC-Biotin, NHS-LC-LC-Biotin, available online at http://www.piercenet.com/files/0237dh4.pdf). Briefly, 5 mg of anti-E. coli polyclonal antiserum was incubated overnight with a 75:1 mol:mol ratio of biotinamidocaproic acid N-hydroxysuccinimide ester (Pierce Biotechnology, Rockford, Ill.) in 100 mM phosphate buffer, pH 7.5. The reaction mixture was dialyzed to remove free biotin, yielding biotinylated anti-E. coli polyclonal antiserum. To prepare streptomycin-conjugated anti-E. coli polyclonal antiserum, 5 mg streptomycin sulfate was reacted with 0.9 mg of 3,3'-N-[e-Maleimidocaproic acid]hydrazide (EMCH; Pierce Biotechnology, Rockford, Ill.) in $H_2O$, yielding streptomycin-EMCH. Anti-E. coli polyclonal antiserum (5 mg) was incubated for 1 hr with 2 mg of Traut's reagent (2-iminothiolane, Sigma Chemical, St. Louis, Mo.) in 100 mM phosphate buffer, pH 7.5, followed by addition of the streptomycin-EMCH. After 20 hrs of incubation, the reaction was dialyzed to remove excess small-molecule reagents, yielding streptomycin-conjugated anti-E. coli polyclonal antiserum.

Production of signal particles. Colloidal gold sol was prepared as previously described (Beesley J (1989) "Colloidal Gold. A new perspective for cytochemical marking". Royal Microscopical Society Handbook No 17. Oxford Science Publications. Oxford University Press.). Streptavidin (50 ug; Sigma Chemical, St. Louis, Mo.) was added to 5 ml of 1% w/w gold sol for 1 hr. Gold sol was then blocked with 1% bovine serum albumin (BSA, Sigma Chemical, St. Louis, Mo.) and washed by centrifugation and resuspension to original volume in 100 mM Tris buffer, pH 7.5. As an alternative, streptavidin-conjugated blue-dyed 0.1 um-diameter latex particles (1% suspension; Bangs Laboratories, Fishers, Ind.) were used.

Figure 8:
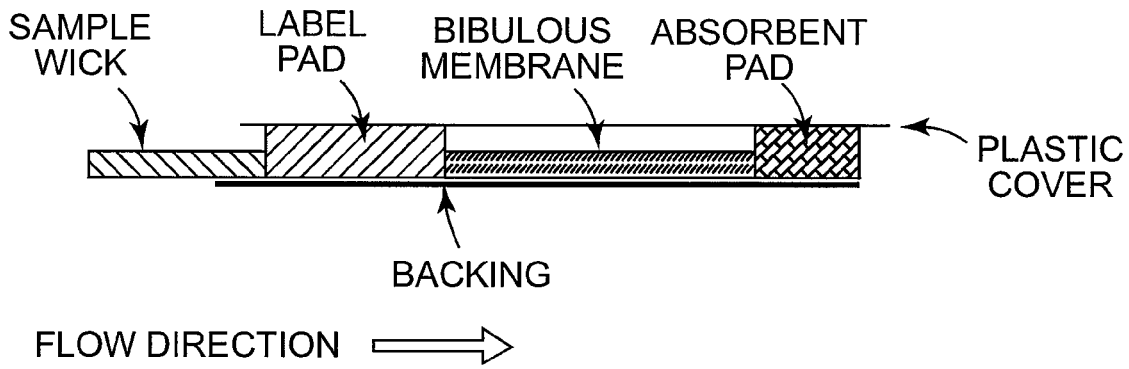
FIG. 8 is an immunochromatographic test strip diagram.
Figure 9:
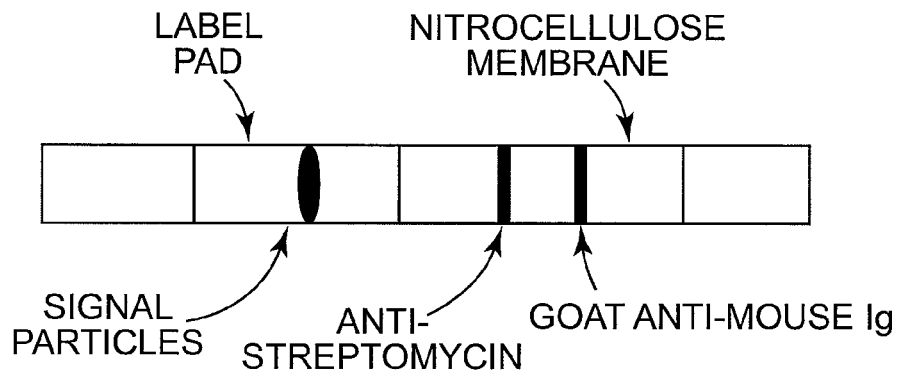
FIG. 9 shows placement of reagents on the immunochromatographic test strip of FIG. 8.

Production of immunochromatographic test strips. Immunochromatographic test strips were prepared as described in several publications, including (Short Guide for Developing Immunochromatographic Test Strips (Bedford, Mass.: Millipore Corp., 1996)), (Weiss, A. Concurrent engineering for lateral-flow diagnostics. IVD Technology, November 1999, p. 48), (M A Harvey, Optimization of Nitrocellulose Membrane Based Immunoassays (Keene, N. H.: Schleicher & Schuell, 1991), (Guide to Building Molecular and Immunodiagnostic Device Platforms (Keene, N. H.: Schleicher & Schuell, 1997). Test strip chromatographic media included Hi-Flow plastic-backed nitrocellulose membrane (Millipore Corp., Bedford, Mass.); Hi-Flow glass fiber media (Millipore Corp., Bedford, Mass.), acrylic plastic protective cover (G&L, San Jose, Calif.), and adhesive-coated plastic backing (G&L, San Jose, Calif.), arranged in accordance to FIG. 8. The dimensions of each immunochromatographic test strip were 6.3 cm long×0.4 cm wide. A 5 mg/ml solution of anti-streptomycin monoclonal antibody CH-2013 (Biodesign International, Saco, Me.) was deposited in a 1 mm-wide stripe across the immunochromatographic test strip and allowed to dry. A 5 mg/ml solution of purified goat anti-mouse-immunoglobulin antiserum was deposited in another 1 mm-wide stripe across the immunochromatographic test strip and allowed to dry. The position of the two stripes is shown in FIG. 9. Streptavidin-gold sol, prepared as in Step 2 above, was dispensed onto the glass fiber portion of the immunochromatographic test strip at 10 ul/cm of width and allowed to dry.

Figure 10:
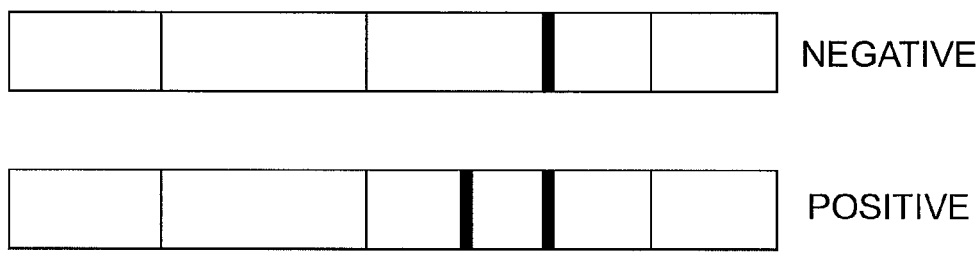
FIG. 10 provides the readout of results on the immunochromatographic test strip.

Performance of the test. Escherichia coli (strain ATCC 700620) were cultured according to standard methods (D. H. Bergey, John G. Holt, Noel R. Krieg, and Peter H. A. Sneath, eds. Bergey's Manual of Determinative Bacteriology, 9th ed., Baltimore: Williams & Wilkins, 1993; Also, ATCC instructions for culture, http://www.atcc.org/) and used to spike samples of water. The concentration of bacteria was determined by heterotrophic plate count. To 150 ul of a water sample was added 0.25 ug of biotinylated anti-E. coli polyclonal antiserum and 0.25 ug of streptomycin-conjugated anti-E. coli polyclonal antiserum, both prepared as in Step 1 above. The mixture was allowed to incubate for 5 minutes, and an immunochromatographic test strip (prepared as in Step 3 above) was inserted into the mixture, with the glass fiber end of the strip coming into contact with the liquid sample. The sample was allowed to migrate through the test strip for 10 minutes, with colored lines appearing at the location of one or both of the two deposited lines of antibody. Results were interpreted according to FIG. 10 (one line—negative, two lines—positive).

Results. Test strip results from several spiked samples are presented in Table 1. Samples with bacterial concentrations $\geq 5 \times 10^4$ CFU/ml gave positive results, and samples with bacterial concentrations $\geq 5 \times 10^3$ CFU/ml gave negative results, indicating a detection limit for this test of ~$10^4$ CFU/ml.

TABLE 1

Results of Test Strips of Example 1.

| Sample # | CFU/ml | Test Strip Result |
|---|---|---|
| 1 | 0 | Negative |
| 2 | 50 | Negative |
| 3 | 500 | Negative |
| 4 | $5 \times 10^3$ | Negative |
| 5 | $5 \times 10^4$ | Positive |
| 6 | $5 \times 10^5$ | Positive |
| 7 | $5 \times 10^6$ | Positive |

Example 2

Detection of a Single Analyte with a Single-Label System

The following example describes the detection of the bacterium Escherichia coli with a modification of the method of Example 1. In this example, a single-label system is used—streptomycin. The label-binding molecule is a monoclonal antibody to streptomycin. In this example, the signal particles are directly attached to the anti-E. coli polyclonal antiserum, which is contacted to the sample at the same time as the streptomycin-conjugated anti-E. coli polyclonal antiserum.

Production of labelled anti-E. coli antibodies. Anti-E. coli polyclonal antiserum and streptomycin-conjugated anti-E. coli polyclonal antiserum were produced as described in Example 1.

Production of signal particles. Colloidal gold sol was prepared as previously described (Beesley J (1989) "Colloidal Gold. A new perspective for cytochemical marking". Royal Microscopical Society Handbook No 17. Oxford Science Publications. Oxford University Press.). Alternatively, colored 0.1 um-diameter polystyrene latex particles (1% suspension; Bangs Laboratories, Fishers, Ind.) were used. Anti-E. coli polyclonal antiserum (50 ug) was added to 5 ml of 1% w/w color particles for 1 hr. The reaction was then blocked with 1% bovine serum albumin (BSA, Sigma Chemical, St. Louis, Mo.) and washed by centrifugation and resuspension to original volume in 100 mM Tris buffer, pH 7.5.

Production of immunochromatographic test strips. Immunochromatographic test strips were prepared as described in Example 1.

Performance of the test. Escherichia coli were cultured according to standard methods (D. H. Bergey, John G. Holt, Noel R. Krieg, and Peter H. A. Sneath, eds. Bergey's Manual of Determinative Bacteriology, 9th ed., Baltimore: Williams & Wilkins, 1993; Also, ATCC instructions for culture, http://www.atcc.org/) and used to spike samples of water. The concentration of bacteria was determined by heterotrophic plate count. To 150 ul of a water sample was added 0.25 ug of streptomycin-conjugated anti-E. coli polyclonal antiserum and 10 ul of anti-E. coli polyclonal antiserum-conjugated signal particles, both prepared as described in Steps 1 and 2 above. The mixture was allowed to incubate for 5 minutes, and an immunochromatographic test strip (prepared as in Step 3 above) was inserted into the mixture, with the glass fiber end of the strip coming into contact with the liquid sample. The sample was allowed to migrate through the test strip for 10 minutes, with colored lines appearing at the location of one or both of the two deposited lines of antibody. Results were interpreted according to FIG. 10 (one line—negative, two lines—positive).

Results. Test strip results from several spiked samples are presented in Table 2. Samples with bacterial concentrations $\geq 7.2 \times 10^4$ CFU/ml gave positive results, and samples with bacterial concentrations $\geq 7.2 \times 10^3$ CFU/ml gave negative results, indicating a detection limit for this test of ~$10^4$ CFU/ml.

TABLE 2

Results of Test Strips of Example 2.

| Sample # | CFU/ml | Test Strip Result |
|---|---|---|
| 1 | 0 | Negative |
| 2 | 72 | Negative |
| 3 | 720 | Negative |
| 4 | $7.2 \times 10^3$ | Negative |
| 5 | $7.2 \times 10^4$ | Positive |
| 6 | $7.2 \times 10^5$ | Positive |

Example 3

Alternative for Detection of a Single Analyte with a Single-Label System

The following example describes the detection of the bacterium Escherichia coli with another modification of the method of Example 1. In this example, a single-label system is used—streptomycin. The label-binding molecule is a monoclonal antibody to streptomycin. In this example, the signal particles are directly attached to the monoclonal antibody to streptomycin, which is contacted to the sample at the same time as, or after, the contact the streptomycin-conjugated anti-E. coli polyclonal antiserum.

Production of labelled anti-E. coli antibodies. Anti-E. coli polyclonal antiserum and streptomycin-conjugated anti-E. coli polyclonal antiserum were produced as described in Example 1.

Production of signal particles. Colloidal gold sol was prepared as previously described (Beesley J (1989) "Colloidal Gold. A new perspective for cytochemical marking". Royal Microscopical Society Handbook No 17. Oxford Science Publications. Oxford University Press.). Alternatively, colored 0.1 um-diameter polystyrene latex particles (1% suspension; Bangs Laboratories, Fishers, Ind.) were used. Purified monoclonal antibody to streptomycin (50 ug) was added to 5 ml of 1% w/w color particles for 1 hr. The reaction was then blocked with 1% bovine serum albumin (BSA, Sigma Chemical, St. Louis, Mo.) and washed by centrifugation and resuspension to original volume in 100 mM Tris buffer, pH 7.5.

Production of immunochromatographic test strips. Immunochromatographic test strips were prepared as described in Example 1, with the following modification. In place of CH-2013 monoclonal antibody to streptomycin, anti-E. coli polyclonal antiserum was deposited in a 1 mm-wide stripe across the immunochromatographic test strip and allowed to dry. All other procedures for preparation of immunochromatographic test strips were the same as in Example 1.

Performance of the test. Escherichia coli were cultured according to standard methods (D. H. Bergey, John G. Holt, Noel R. Krieg, and Peter H. A. Sneath, eds. Bergey's Manual of Determinative Bacteriology, 9th ed., Baltimore: Williams & Wilkins, 1993; Also, ATCC instructions for culture, http://www.atcc.org/) and used to spike samples of water. The concentration of bacteria was determined by heterotrophic plate count. To 150 ul of a water sample was added 0.25 ug of streptomycin-conjugated anti-E. coli polyclonal antiserum and 10 ul of anti-E. coli polyclonal antiserum-conjugated signal particles, both prepared as described in Steps 1 and 2 above. The mixture was allowed to incubate for 5 minutes, and an immunochromatographic test strip (prepared as in Step 3 above) was inserted into the mixture, with the glass fiber end of the strip coming into contact with the liquid sample. The sample was allowed to migrate through the test strip for 10 minutes, with colored lines appearing at the location of one or both of the two deposited lines of antibody. Results were interpreted according to FIG. 10 (one line—negative, two lines—positive).

Results. Test strip results from several spiked samples are presented in Table 3. Samples with bacterial concentrations $\geq 2.8 \times 10^5$ CFU/ml gave positive results, and samples with bacterial concentrations $\geq 2.8 \times 10^4$ CFU/ml gave negative results, indicating a detection limit for this test of ~$10^5$ CFU/ml.

TABLE 3

Results of Test Strips of Example 3.

| Sample # | CFU/ml | Test Strip Result |
|---|---|---|
| 1 | 0 | Negative |
| 2 | 28 | Negative |
| 3 | 280 | Negative |
| 4 | $2.8 \times 10^3$ | Negative |
| 5 | $2.8 \times 10^4$ | Negative |
| 6 | $2.8 \times 10^5$ | Positive |

Example 4

Detection of Multiple Analytes with a Double-Label System

The following example describes the detection of multiple bacteria with a modification of the method of Example 1. In many microbiological testing applications, it is desirable to know if any of a multiplicity of bacterial types is present in a sample, without necessarily identifying the species being detected. One such application is an assay to test the effectiveness of a disinfection protocol. This example of the invention describes a method to use a mixture of antibodies to detect a range of indicator bacteria for contamination of beach water by sewage or storm runoff. Various studies have shown that *E. coli* or *Enterococcus* spp. are both useful indicator bacteria to identify the potential presence of bacteria that cause recreational water illnesses (RWI) in swimmers (Griffith, J. and S. B. Weisberg. 2006. *Evaluation of Rapid Microbiological Methods for Measuring Recreational Water Quality*. Southern California Coastal Water Research Project, Westminster, Calif.). In a detection assay for bacteria in beachwater, it is desirable to detect a wide range of strains of both *E. coli* and *Enterococcus* spp. The presence of a significant number of any of the strains of either *E. coli* or *Enterococcus* spp. would indicate potentially contaminated water.

This example describes the use of a mixture of antisera with narrow specificities to achieve a rapid immunoassay test with broad specificity for the desired range of bacteria. Antibodies were produced with specificity for *E. coli*, and other antibodies for *Enterococcus* spp.; a total of three separate antisera were used for this assay method. In this example, a double-label system is used—one label is biotin and the other streptomycin. The label-binding molecules are streptavidin and a monoclonal antibody to streptomycin. Neither label is expected to occur naturally in beachwater at a significant concentration, minimizing the chances of matrix interferences.

Production of labelled anti-*E. coli* antibodies. Anti-*E. coli* polyclonal antiserum was produced as described in Example 1. Two other antisera were produced by parallel methods, for *Enterococcus faecium* (strain ATCC 12952) and *Enterococcus faecalis* (strain ATCC 10471) Each serum was conjugated to biotin and streptomycin as described in Example 1, Step 1.

Production of signal particles. Streptavidin-conjugated colloidal gold sol or polystyrene latex was prepared as described in Example 1, Step 2.

Production of immunochromatographic test strips. Immunochromatographic test strips were prepared as described in Example 1, Step 3.

Performance of the test. *E. coli, Enterococcus faecium*, and *Enterococcus faecalis* were cultured and used to spike samples of water. The concentration of bacteria was determined by heterotrophic plate count. To 150 ul of a water sample was added 0.15 ug of each biotinylated polyclonal antiserum and 0.15 ug of each streptomycin-conjugated polyclonal antiserum. The mixture was allowed to incubate for 5 minutes, and an immunochromatographic test strip (prepared as in Step 3 above) was inserted into the mixture, with the glass fiber end of the strip coming into contact with the liquid sample. The sample was allowed to migrate through the test strip for 10 minutes, with colored lines appearing at the location of one or both of the two deposited lines of antibody. Results were interpreted according to FIG. 10 (one line—negative, two lines—positive).

Results. Test strip results from several spiked samples are presented in Table 4. Samples with total bacterial concentrations $\geq 1 \times 10^4$ CFU/ml gave positive results, and samples with bacterial concentrations $\geq 9 \times 10^3$ CFU/ml gave negative results, indicating a detection limit for this test of $\sim 10^4$ CFU/ml. There was some variation seen in the sensitivity for each individual species of bacteria, but, overall, the result of the test showed a high correlation with the total bacterial concentration being above or below $1 \times 10^4$ CFU/ml.

TABLE 4

Results of Test Strips of Example 4.

| Sample # | CFU/ml *E. coli* | CFU/ml *Enterococcus faecium* | CFU/ml *Enterococcus faecalis* | Test Strip Result |
|---|---|---|---|---|
| 1 | 0 | 0 | 0 | Negative |
| 2 | 55 | 67 | 94 | Negative |
| 4 | 550 | 670 | 940 | Negative |
| 5 | 55 | 670 | 94 | Negative |
| 6 | 5500 | 0 | 0 | Negative |
| 7 | 0 | 6700 | 0 | Negative |
| 8 | 0 | 0 | 9400 | Positive |
| 9 | 5500 | 670 | 940 | Negative |
| 10 | 550 | 6700 | 940 | Negative |
| 11 | 550 | 670 | 9400 | Positive |
| 12 | 5500 | 6700 | 940 | Positive |
| 13 | 5500 | 0 | 9400 | Positive |
| 14 | 0 | 6700 | 9400 | Positive |
| 15 | 5500 | 6700 | 0 | Positive |
| 16 | 55000 | 6700 | 0 | Positive |
| 17 | 0 | 0 | 94000 | Positive |
| 18 | 55000 | 0 | 0 | Positive |
| 19 | 0 | 67000 | 0 | Positive |
| 20 | 55000 | 67000 | 0 | Positive |
| 21 | 55000 | 0 | 94000 | Positive |
| 22 | 55000 | 67000 | 94000 | Positive |

Example 5

Alternative Method for Detection of Multiple Analytes with a Double-Label System The following example describes a modification of the detection of multiple bacteria with the method of Example 4. This example of the invention describes another method to use a mixture of antibodies to detect *E. coli, Enterococcus faecium*, and *Enterococcus faecalis* in aqueous samples.

This example also uses three separate antisera and a double-label system, although single-label systems would also be appropriate. The label-binding molecules are streptavidin and a monoclonal antibody to streptomycin. The modification from Example 4 is in the sequence of addition of reagents to achieve the same complex formation. In this Example 5, the strepatvidin-conjugated colloidal gold sol or polystyrene latex is not deposited on the immunochromatographic test strip, rather it is added as a liquid reagent to the reaction mix containing the sample and the antibody mixture.

Production of labelled anti-*E. coli* antibodies. Anti-*E. coli* polyclonal antiserum, anti-*Enterococcus faecium* polyclonal antiserum, and anti-*Enterococcus faecalis* polyclonal antiserum were produced as described in Examples 1 and 4. Each serum was conjugated to biotin and streptomycin as described in Example 1, Step 1.

Production of signal particles. Streptavidin-conjugated colloidal gold sol or polystyrene latex was prepared as described in Example 1, Step 2. Streptavidin-conjugated polystyrene latex was kept as a liquid suspension. Streptavidin-conjugated colloidal gold sol was lyophilized and kept dry under vacuum until use. Prior to use in the testing of samples, lyophilized streptavidin-conjugated colloidal gold sol was rehydrated to original volume with distilled water.

Production of immunochromatographic test strips. Immunochromatographic test strips were prepared as described in Example 1, Step 3, with the following modification: streptavidin-gold sol was not dispensed onto the glass fiber portion of the immunochromatographic test strip.

Performance of the test. *E. coli, Enterococcus faecium*, and *Enterococcus faecalis* were cultured and used to spike samples of water. The concentration of bacteria was determined by heterotrophic plate count. To 150 ul of a water sample was added 0.15 ug of each biotinylated polyclonal antiserum and 0.15 ug of each streptomycin-conjugated polyclonal antiserum. The mixture was allowed to incubate for 5 minutes. Following the incubation, 15 ul of streptavidin-conjugated colloidal gold sol or streptavidin-conjugated polystyrene latex was added to the reaction mix, and allowed to incubate for 5 minutes. An immunochromatographic test strip (prepared as in Step 3 above) was inserted into the mixture, with the glass fiber end of the strip coming into contact with the liquid sample. The sample was allowed to migrate through the test strip for 10 minutes, with colored lines appearing at the location of one or both of the two deposited lines of antibody. Results were interpreted according to FIG. 10 (one line—negative, two lines—positive).

Results. Test strip results from several spiked samples are presented in Table 5 Samples with total bacterial concentrations $\geq 1.1 \times 10^4$ CFU/ml gave positive results, and samples with bacterial concentrations $\geq 4 \times 10^3$ CFU/ml gave negative results, indicating a detection limit for this test of $\sim 10^4$ CFU/ml. There was some variation seen in the sensitivity for each individual species of bacteria, but, overall, the result of the test showed a high correlation with the total bacterial concentration being above or below $1 \times 10^4$ CFU/ml.

TABLE 5

Results of Test Strips of Example 5.

| Sample # | CFU/ml E. coli | CFU/ml Enterococcus faecium | CFU/ml Enterococcus faecalis | Test Strip Result |
|---|---|---|---|---|
| 1 | 0 | 0 | 0 | Negative |
| 2 | 400 | 720 | 290 | Negative |
| 3 | 4000 | 720 | 290 | Negative |
| 4 | 4000 | 7200 | 290 | Positive |
| 5 | 4000 | 7200 | 290 | Positive |
| 6 | 400 | 7200 | 2900 | Positive |
| 7 | 400 | 720 | 2900 | Negative |
| 8 | 4000 | 7200 | 2900 | Positive |

Although the present invention has been described with reference to preferred embodiments, persons skilled in the art will recognize that changes may be made in form and detail without departing from the spirit and scope of the invention.

All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

I claim:

1. A device for the detection of an analyte in a sample solution, comprising:
   a) components comprising an analyte-binding molecule having a first label and a second analyte-binding molecule having a second label, wherein the combination of the components is capable of forming a complex when contacted by fluid comprising the analyte;
   b) a first-label binding molecule comprising a signal reagent, capable of binding the complex of (a); and
   c) a solid support comprising a capture zone, the capture zone comprising a binding molecule suitable to bind to the second label, wherein the complex of (a) is in fluid communication with the binding molecule of (b) and with the capture zone.

2. The device of claim 1, wherein the first or second analyte-binding molecule is an antibody, an aptamer, a receptor, an antibody fragment, or a polynucleotide.

3. The device of claim 1, wherein the first or second label is a hapten or polypeptide and the first- or second-label-binding molecule is an antibody, an antibody fragment, or a receptor capable of binding the hapten or polypeptide.

4. The device of claim 1, wherein at least one member of a set that includes the analyte-binding molecule having a first label, the second analyte-binding molecule having a second label, and the first-label-binding molecule comprising a signal reagent is deposited on the solid support.

5. A method of detecting an analyte in solution, comprising the steps of:
   a) contacting a solution suspected of comprising the analyte with a first analyte-binding molecule having a first label and a second analyte-binding molecule having a second label, wherein the combination of the binding molecules is capable of forming a complex (a) when contacted by fluid comprising an analyte;
   b) contacting the solution containing the complex (a) with a first-label-binding molecule comprising a signal reagent;
   c) flowing the solution comprising the complex (a) and the first-label-binding molecule comprising a signal reagent through a chromatographic test strip to a capture zone, comprising a binding molecule suitable to bind to the second label; and
   d) determining the presence of the analyte in the solution by the presence of the signal reagent in the capture zone of the chromatographic test strip.

6. The method of claim 5, wherein the first or second analyte-binding molecule is an antibody, an aptamer, a receptor, an antibody fragment, or a polynucleotide.

7. The method of claim 5, wherein the first or second label is a hapten or polypeptide and the first- or second-label-binding molecule is an antibody, an antibody fragment, or a receptor capable of binding the hapten or polypeptide.

8. The method of claim 5, wherein the presence or absence of the analyte is determined visually or spectrophotometrically.

9. The method of claim 5, wherein the second analyte-binding molecule is the same as the first analyte-binding molecule.

10. The device of claim 1, wherein the second analyte-binding molecule is the same as the first analyte-binding molecule.

* * * * *